(12) United States Patent
Sitka

(10) Patent No.: US 6,330,572 B1
(45) Date of Patent: Dec. 11, 2001

(54) HIERARCHICAL DATA STORAGE MANAGEMENT

(75) Inventor: Larry Sitka, Stillwater, MN (US)

(73) Assignee: Imation Corp., Oakdale, MN (US)

( * ) Notice: Subject to any disclaimer, the term of this patent is extended or adjusted under 35 U.S.C. 154(b) by 0 days.

(21) Appl. No.: 09/354,280

(22) Filed: Jul. 15, 1999

Related U.S. Application Data

(60) Provisional application No. 60/092,853, filed on Jul. 15, 1998.

(51) Int. Cl.[7] .................................................. G06F 17/30
(52) U.S. Cl. ........................ 707/205; 203/204; 203/104; 203/100
(58) Field of Search ..................................... 707/104, 100, 707/201, 205, 203–204

(56) References Cited

U.S. PATENT DOCUMENTS

| | | |
|---|---|---|
| 5,276,860 | 1/1994 | Fortier et al. . |
| 5,276,867 | 1/1994 | Kenley et al. . |
| 5,317,728 | 5/1994 | Tevis et al. . |
| 5,367,698 | 11/1994 | Webber et al. . |
| 5,537,585 * | 7/1996 | Blickenstaff et al. ............... 707/100 |
| 5,557,790 | 9/1996 | Bingham et al. . |
| 5,579,507 | 11/1996 | Hosouchi et al. . |
| 5,579,516 * | 11/1996 | Van Maren et al. ................. 395/601 |
| 5,584,008 | 12/1996 | Shimada et al. . |
| 5,778,395 * | 7/1998 | Whiting et al. ....................... 707/204 |
| 5,784,646 | 7/1998 | Sawada . |
| 5,822,780 | 10/1998 | Schutzman . |
| 5,832,522 | 11/1998 | Blickenstaff et al. . |
| 5,878,410 * | 3/1999 | Zbikowski et al. ....................... 707/2 |
| 5,918,229 * | 6/1999 | Davis et al. ............................ 707/10 |
| 5,991,753 | 11/1999 | Wilde . |
| 6,026,474 * | 2/2000 | Carter et al. ......................... 711/202 |
| 6,108,713 * | 1/2000 | Coli et al. ................................ 705/2 |

FOREIGN PATENT DOCUMENTS 0 474 395 A2  11/1992  (EP) .

OTHER PUBLICATIONS

"Hierarchical View of Filesets," IBM Technical Disclosure Bulletin, vol. 36(5):167 (1993).

Shiers, J.D., "Data Management at Cern: Current Status and Future Trends," http://www.computer.org/conferences/mss95/shiers/shiers.htm, Cern, Geneva, Switzerland, pp. 1–11 (1995).

"Graphical User Interface for the Distributed Computing Environment," IBM Technical Disclosure Bulletin, vol. 38(1):409–410 (1995).

* cited by examiner

*Primary Examiner*—Hosain T. Alam
*Assistant Examiner*—Cam-Y Truong
(74) *Attorney, Agent, or Firm*—William D. Bauer

(57) ABSTRACT

A system and method for managing the storage of files within an HSM system incorporate an architecture and methodology that facilitate the storage and retrieval of large image files as part of an overall image processing workflow. In particular, the system and method may find ready application in a workflow that involves the processing of groups of images associated with particular customers, projects, or transactions, and may act as a storage server for a client application that implements the workflow. The system and method may be useful, for example, in handling the storage of images uploaded from scanned photographic film, or digital images submitted to a photo-processing shop by amateur or professional photographers. In this case, the client application can be a photo-processing application that could provide for various media formats, sizes, and quantities of image reproductions for a consumer. As another example, the system and method may be useful in handling the storage of medical diagnostic images associated with a particular medical patient or study. In this case, the client application could be a picture archival communication system (PACS) that manages the archival of imagery for viewing by physicians. Further, the system and method may be useful in handling the storage of images associated with particular printing jobs, e.g., for publishers, advertising customers, and the like. In this case, the client application could be a digital prepress workflow application.

32 Claims, 8 Drawing Sheets

HIERARCHICAL DATA STORAGE MANAGEMENT

This application claims priority from U.S. Provisional Application Serial No. 60/092,853, filed Jul. 15, 1998, the entire content of which is incorporated herein by reference.

TECHNICAL FIELD

The present invention relates to data storage and, more particularly, to systems and methods for hierarchical storage management.

BACKGROUND

Hierarchical storage management (HSM) systems allow the managed storage of data files among a variety of media such as magnetic hard disks, magneto-optic disks, and magnetic tape. The various media differ in access time, capacity, and cost. Thus, HSM systems typically are configured such that files that are accessed more frequently or created more recently are stored on "short-term" media having the shortest access time. Short-term media often includes a group of magnetic disks, which may be arranged as a redundant array of independent disks (RAID). Files that are accessed less frequently, created less recently, or have larger sizes are stored on "long-term" media having longer access times and larger storage capacities. Long-term media in an HSM system may include rewritable optical disks and magnetic tape media, which can be arranged in a jukebox of magneto-optical disks or a tape library, respectively.

Existing HSM systems typically allocate individual files across the hierarchy of storage media based on frequency of use, creation date, or file size, as discussed above. Accordingly, HSM systems generally seek to avoid excessive access delays in retrieving information that is likely to be accessed most often or most frequently by users. As new files are generated, the system stores the files on the short-term media using a "best-fit" approach. In this manner, the system distributes files across the short-term media in order to minimize wasted storage space. Thus, each file may be stored on a different medium in order to most efficiently manage storage space.

A central database maintains the storage location of each file within the HSM system. If users do not request a particular file for an extended period of time, the system automatically migrates the corresponding file to the longer-term storage media and updates the file location database. Again, the system distributes the relocated file across the long-term storage media in a manner calculated to minimize wasted storage space. For image files, an HSM system may store a number of copies at different display resolutions and on different media to facilitate identification and retrieval by a user. When a user requests a particular file, the system accesses the database to determine the current location of the file. If the desired files reside on longer-term storage media, the system automatically retrieves the files and moves them to the short-term media. If some of the media is not currently loaded into the longer-term storage device, the system generates a request for personnel to physically locate the media and load it into the storage device.

SUMMARY

The present invention is directed to a system and method for managing the storage of files within an HSM system. The system and method are especially useful in managing the storage of larger files that include graphic imagery. The system and method may incorporate an architecture and methodology that facilitate the storage and retrieval of image files as part of an overall image processing workflow. In particular, the system and method may find ready application in a workflow that involves the processing of groups of images associated with particular customers, projects, or transactions, and may act as a storage server for a client application that implements the workflow.

The system and method may be useful, for example, in handling the storage of images uploaded from scanned photographic film, or digital images submitted to a photo-processing shop by amateur or professional photographers. In this case, the client application can be a photo-processing application that could provide for various media formats, sizes, and quantities of image reproductions for a consumer. As another example, the system and method may be useful in handling the storage of medical diagnostic images associated with a particular medical patient or study. In this case, the client application could be a picture archival communication system (PACS) that manages archival of imagery for viewing by physicians. Further, the system and method may be useful in handling the storage of images associated with particular printing jobs, e.g., for publishers, advertising customers, and the like. In this case, the client application could be a digital prepress workflow application.

The system and method may incorporate a number of architectural and functional features capable of improving overall economy of storage while maintaining workflow efficiency for the user, as described below. Such features may be used together or independently of one another according to the needs of the particular storage and workflow applications.

As an example, a fileset feature can be provided that permits grouping of images associated with a particular customer, project, or transaction. The fileset feature allows a user to group files into a logical collection, and perform operations on the files as a group. Moreover, filesets can be configured to have their member files reside together on common media, so that operations on the fileset such as archival, migration, retrieval, and deletion can be performed significantly faster than operating on the individual files, which might otherwise be distributed across multiple media.

In this manner, the system and method are capable of intelligently grouping images for storage together on common storage media to alleviate excessive access times in retrieving the images. Thus, the fileset feature can be used to avoid the scattering of associated images across diverse storage media having different access times, and resulting delays in incorporating such images into the workflow of the client application. In addition, a fileset can be configured such that activity on an individual file member triggers the same activity on the other file members of the fileset.

Also, a media independence feature can be incorporated whereby data can be stored on particular volumes without knowledge of the media type of the volume. In this case, the system and method provide an application programming interface that is substantially identical for all media types, for both direct access and sequential access, and for removable and non-removable media.

Along with media independence, the system and method may further include a feature that allows the storage volumes to support self-describing media. Normally, an inventory of the contents of a volume are maintained as entries in a database. This self-describing media feature provides the capability to reconstruct the database entries for the files stored on a volume when a volume is physically moved to another system that is not on the same network. A volume may be physically moved, for example, when the database has been corrupted, when identifying unlabeled or mislabeled media from shelf storage, or when a volume is moved to a remote server.

The self-describing media feature can be implemented by storing volume metadata on each physical volume and by storing file metadata for each data file on the same physical volume on which the data file is stored. Thus, each file may include two files: a blob file with the actual file contents and a metadata file with identifying information. The metadata provides sufficient information to rebuild an inventory of the contents of a volume without access to the original file location database.

The metadata can be useful in tracking volumes and files, verification of the identities of loaded volumes, and database recovery. The metadata can be specified by a client application and can be substantially transparent to the storage management server, providing information known to the client application such as the particular client applications and users associated with the volume or file.

For unique identification of volumes and files, the metadata may incorporate a global unique identifier (guid) that is unique on a single server, as well as across a multi-server system. Also, a guid can be generated for each storage device. The guid can be used to track the location of a volume or file in the event the volume is moved across the system, or the file is moved across the various media volumes on a server or across the system. The guid for a particular file can be generated by the storage management system, but preferably is generated by the client application along with other metadata useful in referencing the file.

A client application programming interface (API) also can be included to provide a number of features to a programmatic user of the system and method. In particular, the client API may allow for file storage and retrieval that is either directed by a user to or from a particular collection of media, or is undirected. Further, the client API can facilitate file grouping by allowing fileset creation and modification to generate logical collections of files.

The client API also can be used to provide restricted, password-protected logons to distributed server systems, user and user group permissions on files, and a set of privileged, administrator-only functions. In a network configuration, in particular, the client API can provide additional levels of security. For example, the server system can be protected first by a firewall, second by a HSM system server logon and password, third by file system access control lists, such as the NTFS ACL provided by the Windows NT operating system, and finally by database server logon and password. In addition, the client API enables policy creation and modification to provide settings for determining default behavior of the storage management function and its background agents.

System configuration also can be managed via the client API, such that hardware and software setup is API-configurable. With the client API, the server systems can be local or remote. In particular, the client API implementation can be made to communicate through industry-standard TCP/IP protocols to distributed server systems running on any machine that is IP-addressable by the machine on which an application runs.

The policies implemented by an administrator govern several behavioral aspects of the data and media management functions. For example, policies can be defined to control the set of media to be used for storage of files associated with particular clients, the movement and replication of the files to other sets of media, peer-to-peer data movement between servers, the timing of data movement and replication, maximum file size allowed for various sets of media, retention intervals on various sets of media, versioning, fileset behaviors, media lifetime, tape retensioning, tape compaction, automated media replacement, and automated media upgrades.

Further, the system and method may employ a unique algorithm for migration of data. This algorithm migrates data based on four distinct watermark levels: the deletion high-watermark and low-watermark, and the copy high-watermark and low-watermark. Different combinations of values for these watermarks allow the single migration algorithm to function in various ways, based on customer requirements. Three of the common scenarios that can be supported by the migration algorithm are (1) watermark migration with deletion; (2) copy without deletion and (3) copy immediately.

For scenario (1), files are copied to another storage device when a high-watermark is reached, and deleted from one storage level soon after they are copied to another level. This keeps large areas of space available to handle burst activity, and allows migration to occur in batches and be performed at low-load intervals. For scenario (2), files are copied to another storage device when a high-watermark is reached, but not deleted from a storage until space on that storage is low. This can improve caching by retaining files for a longer period of time, but may cause delays during large peak loads while files are being deleted. It also allows migration to occur in batches, and can be performed at low-load intervals. For scenario (3), files are scheduled to be copied soon after they are stored, but not deleted from the storage until space on the storage is low. Here, migration can occur as a continuous, low-priority task.

The system and method also can be configured to provide direct access to the storage function instead of indirect access, e.g., via a SQL server. In particular, the system and method can be arranged to give privileged clients direct read-only access to the file-oriented storage media, with guarantees that the files they specify will remain on that media until they specify otherwise. This provides, for example, the fastest and most direct access to media files that need to be published to web sites, by allowing web servers to publish stored files without having to make a copy of the file elsewhere. This direct access feature also can support specific user-specified file extensions so that applications that trigger on file extension, such as certain web browsers, can use this feature.

As another feature, the system and method may employ an architecture that allows a variety of functions to be allocated to the same or different computer servers in a single storage management system. For example, a central controller, e.g., one per system, handles initial requests from client applications, communicates with library controllers to get volumes mounted, and sets up communication paths to data movers. Library controllers, e.g., one or more per system, handle the movement of media in manual, fixed-media, and/or automated media libraries. Data Movers, e.g., one or more per DSM system, handle the actual movement of data to and from clients and other data movers. A database, e.g., one per DSM system, provides database services to the central controller.

The system and method also can make use of peer-to-peer configurations in which multiple storage management systems can participate as peers in storage management policies. Files that are stored in one system can be migrated or copied to other systems either automatically through administrator-defined policies, or explicitly through client application control. The system and method are configured to maintain file identity, even across multiple servers, by assigning each file a globally unique identifier (guid), as described above.

In order to link web pages to executable programs, the system and method can use an interface referred to as an "automation server." The automation server is created as prescribed by applicable Microsoft specifications. Automation servers having features unique to the system and method of the present invention are (1) a Storage Automation Server; (2) an Exe Automation Server; (3) an Image Tool Automation Server; and (4) an Event Log Automation Server. Storage Automation Server (1) allows a web interface to attach and utilize the client API described above. This interface is portable across any user which requires a web connection to the storage management system. Another unique component is the locking down of individual images on a "Hot" cache to avoid migration. Finally, in storing the images, this automation server specifies a file extension to append to a GUID assigned to the file. This provides great advantage when viewing the images from a browser which does not support any type of image file decoding. For example, when viewing an image, the Netscape Navigator web browser only examines the file name extension such as .jpg, .gif, .tif, etc.

The Exe Automation Server (2) allows a user to kick off and get a return result from any executable program out of a web page. The Image Tool Automation Server (3) allows the calling of image processing tools from a web page. Because web interfaces are page driven and stateless, debugging is extremely difficult. The Event Log Automation Server (4) allows any web interface to log errors encountered from within a web page to the NT event logging facility on any NT server. In this manner, any event at the web interface is translated for programmatic delivery to the NT server, and can be logged for analysis.

The system and method also can be configured to facilitate web-based workflow within an application that invokes the storage management function. From various web pages, and calling the above Automation Servers, for example, an application can scan and/or acquire images from a high speed film scanner, photoscanner, flatbed scanner, PCMCIA cards (digital cameras), or any TWAIN compatible device. Those images then can be compressed into three image file types: (1) a thumbnail image, (2) a screen resolution image, and (3) a high resolution image. All three versions of each image are sent and "checked-in" to the storage management function with a file extension known to be processable by the web browser, e.g., .jpg, via the automation server.

Thus, the client application supporting the web-based workflow converts each acquired image to the supported format such that the user can have direct access to the images maintained by the storage management function within the web browser. No images need to be kept directly within the client database. The screen resolution and thumbnail versions can be "locked" down on the short-term media, such as a RAID, and never allowed to migrate offline to tape. At the same time, the high resolution image may be allowed to migrate according to user-defined migration policies then in effect. In this manner, internet access to the images is as quick as possible. Also, the locked-down images are not stored by the database server, but rather by the HSM server for direct access by the user. By migrating the high resolution image, however, storage costs for RAID are dramatically reduced. In other words, an application can be configured to store images as economically and efficiently as possible using the system and method of the present invention, with the potential for growth of storage capacity being unlimited and scalable.

As a further feature, the present invention may provide a "digital vault" function within a client application. This function can be supported in part by the fileset feature. With this feature, each consumer has his/her own unique digital vault that is accessible as a web page and resembles an electronic safety deposit box. This digital vault contains images that are categorized and stored in folders that are graphically represented on the web page as a set of drawers. Each set consists of a single or multiple set of images that were acquired from one of the acquisition devices described above. On*et could be a single roll of film, another could be a scanned legal document or documents, and another set can be a VHS tape or tape library.

This vault can be password and login protected. All image transmissions can be done under SSL. The vault image viewing is also secured through a virtual directory service, another sequence of logins into the storage management system, a Microsoft SQL Server, and the Windows NT NTFS file system itself. From the vault, the consumer can proof and create his/her own media order. That media order is placed into a "shopping basket" for the consumer, and totaled for payment and shipping. The consumer may also send those images to a third party via internet mail. Those images stored within the vault are set on an aging algorithm where after a predetermined number of days, the images are deleted from the system.

The present invention provides, in one embodiment, a method for storing files comprising assigning the files to filesets, each of the files assigned to a respective one of the filesets sharing one or more common attributes with the other files assigned to the respective fileset, storing the files assigned to the respective fileset together on a common data storage medium, and moving the files assigned to the respective fileset together from the common data storage medium to another common data storage medium.

In another embodiment, the present invention provides a computer-implemented system for storing files comprising a processor that is programmed to assign the files to filesets, each of the files assigned to a respective one of the filesets sharing one or more common attributes with the other files assigned to the respective fileset, control storage of the files assigned to the respective fileset together on a common data storage medium, and control movement of the files assigned to the respective fileset together from the common data storage medium to another common data storage medium.

In an added embodiment, the present invention provides a method for storing files, the method comprising storing the files on data storage media volumes, writing, to each of the media volumes, volume metadata that uniquely describes the respective volume, writing, with each of the files stored on the media volumes, file metadata that uniquely describes the respective file, and moving one or more of the files from one of the media volumes to another of the media volumes, wherein each of the moved files carries with it the file metadata for the respective moved file.

In another embodiment, the present invention provides a computer-implemented system for storing files, the system comprising a processor that is programmed to control storage of the files on data storage media volumes, write, to each of the media volumes, volume metadata that uniquely describes the respective volume, write, with each of the files stored on the media volumes, file metadata that uniquely describes the respective file, and control movement of one or more of the files from one of the media volumes to another of the media volumes, wherein each of the moved files carries with it the file metadata for the respective moved file.

In a further embodiment, the present invention provides a method for storing image files on a hierarchy of data storage media, the method comprising storing a first-resolution copy and a second-resolution copy of an image file together on a first type of media, wherein the second-resolution copy has a higher resolution than the first-resolution copy, migrating the second-resolution copy of the image file to a second type of media according to a migration policy, and preventing migration of the first-resolution copy of the image from the first type of media.

In an added embodiment, the present invention provides a computer-implemented system for storing image files on a hierarchy of data storage media, the system comprising a processor that is programmed to control storage of a first-resolution copy and a second-resolution copy of an image file together on first type of media, wherein the second-resolution copy has a higher resolution than the first-resolution copy, control migration of the second-resolution copy of the image file to a second type of media according to a migration policy, and prevent migration of the first-resolution copy of the image from the first type of media.

In another embodiment, the present invention provides a system for hierarchical storage management comprising a web-based client application that submits images for storage, a storage server that stores the images, and an automation server that converts script-based web events in the client application into programmatic executable commands for execution by the storage server.

In a further embodiment, the present invention provides a system for hierarchical storage management comprising a web-based client application that submits images for storage and requests images from storage for viewing by a user, a storage server that stores and retrieves the images, and an automation server that converts script-based web events in the client application into programmatic executable commands for execution by the storage server, and converts the images submitted by the client application to an image format recognizable by the web browser application on which the client application runs.

Other advantages, features, and embodiments of the present invention will become apparent from the following detailed description and claims.

DESCRIPTION OF DRAWINGS

Like reference numbers and designations in the various drawings indicate like elements.

DETAILED DESCRIPTION

Figure 1:
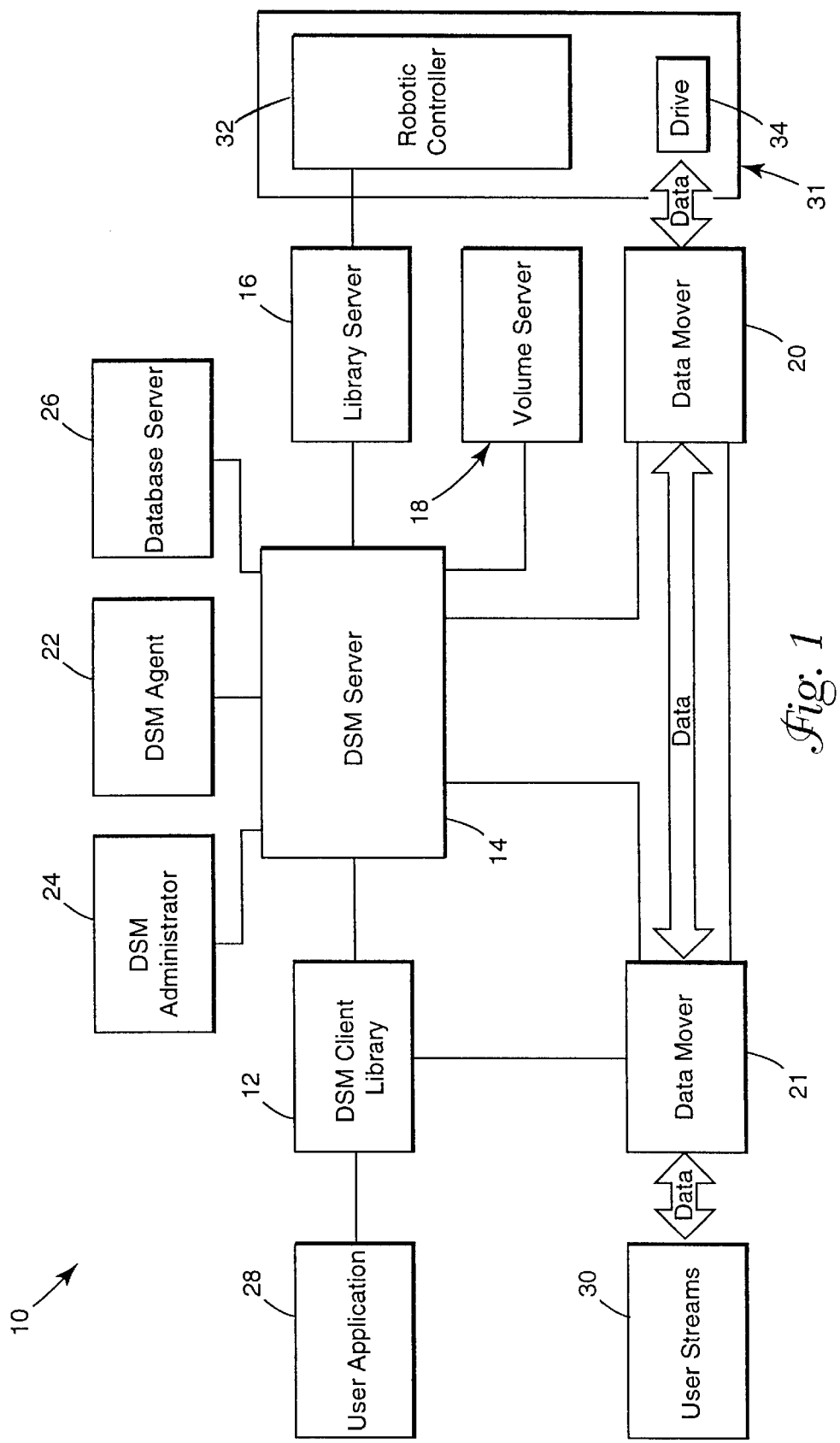
FIG. 1 is a functional block diagram illustrating the architecture of a hierarchical storage management system.

FIG. 1 is a functional block diagram illustrating the architecture of a hierarchical storage management system 10, in accordance with an embodiment of the present invention. System 10 will be described herein as a "directed storage management (DSM)" system inasmuch as it allows a system administrator to introduce, on a selective and reconfigurable basis, significant direction concerning storage management policies including migration. That is, the client and an administrator have the ability to direct a file to a particular location. This differs from a simple hierarchical storage management (HSM) system that handles the selection internally. The difference is that DSM system 10 provides a much broader set of data-movement policies than a typical HSM, and gives a client ways to override those policies. System 10 can be used to implement a method for hierarchical storage management in accordance with an embodiment of the present invention.

The following terms will be used herein to describe the structure and functionality of DSM system 10, and are generally defined as follows. The term "media" refers to a physical piece of data storage media such as a tape, an MO cartridge, a CD, or a hard disk. A "Store" is any collection of like media. The media in a Store can exist in any number of locations, i.e., on shelves, in one or more robotic libraries, or in individual drives. A "freeStore" is a collection of "empty" volumes with the same MediaType. The media in a freeStore can exist in any number of locations, i.e., on shelves, in one or more robotic libraries, or in individual drives. A "File" is a user-defined blob of information that can be stored in DSM system 10. A DSM File will often correspond to a file in a file system. A File may exist in more than one Store at any given time, and will be moved or copied between Stores according to the policies that an administrator has put in place and specific user requests. A "policy" is a rule that governs the automatic movement, i.e., "migration," of files between stores, and removal of files from Stores. A "ticket" or "token" is a unique identifier returned to a client application when a File is stored by DSM system 10. The client will use the ticket for all subsequent references to the File.

With further reference to FIG. 1, DSM system 10 is implemented as a software system having a plurality of logical software components. Such components may include a DSM client library 12, a DSM server process 14, library server process 16, volume server process 18, DSM data mover process 20, client data mover process 21, DSM agent process 22, DSM administrator process 24, and a database server 26.

DSM client library 12 is linked with a client application to provide client-side data mover services. DSM server process 14 operates to control the storage and retrieval of files from various data storage devices. Library server process 16 direct media handling in automated and manual libraries. Volume server process 18 handle mounted volumes and set up data mover process 20, 21 to transfer data. Data mover process 20 move files between DSM clients and mounted DSM volumes. DSM agent process 22 perform routine management functions such as migration and compaction. DSM administrator applications 24 provide a special type of client application for managing DSM system 10. Finally, database server 26 provides robust, recoverable, database storage and services for the other processes.

The above component process 12–26 can reside on a single host machine, or can be distributed across many hosts. The term "process" in this discussion should be interpreted broadly. A process could be a separate application, or one or more threads within an application. FIG. 1 illustrates how the component processes are related, with bold lines indicating networkable interfaces between component processes. Each host machine may be based on any conventional general purpose single- or multi-chip microprocessor such as, for example, a Pentium® processor, a Pentium Pro® processor, an 8051 processor, a MIPS processor, a Power PC® processor, or an Alpha(& processor. Further, the processor can be integrated within a personal computer, computer workstation, or network server to form the host machine, and may be configured to run on any number of operating system environments. The Windows NT operating system platform may be particularly suitable to the storage management tasks carried out by DSM system 10, although the system can be readily adapted for other operating systems such as Unix.

DSM client library 12 may be configured to implement a set of client API (application programming interface) functions that are available to user applications 28. User applications 28 are software applications for manipulation of files stored by DSM system 10. The client API functions can be callable, for example, from C and C++ application programs, and from other languages that can link in C libraries. The basic functions provided by the DSM client library are (1) establish secure connections to DSM server 14; (2) translate client API calls into networkable calls to DSM server 14; and (3) establish client-side data mover process 21 that allow data to move efficiently between user data streams or files 30 and DSM devices and media.

DSM server process 14 is responsible for servicing multiple concurrent requests from its various clients, i.e., user applications 28, DSM agents 22, and DSM administrator applications 24. The basic responsibilities of DSM server process 14 are (a) provide logon and file-access security for its clients; (b) handle concurrent client requests to a given file by providing simultaneous or sequential access depending on the nature of the requests; (c) translate requests for files into requests for data transfer to or from specific media/volume locations; (d) sequence data transfer requests to maximize the utilization and throughput of available devices, while providing a good quality of service to clients; (e) direct the library server process 16 to mount the required volumes at the appropriate points in time; (f) direct the volume server process 18 to establish DSM data mover process 20 for mounted volumes, and connect those processes to client data mover process 21, or other DSM data mover processes, as required; and (g) issue commands to data mover process 20, 21 to effect the requested data transfer.

DSM server process 14 also is responsible for communicating with the DSM administrator process 24 to report errors and effect changes requested by administrators. A DSM server 14 also can communicate with other DSM server process 14 to allow clients to share remote files in a multi-server host environment. A library server process 16 executes on each host that manages removable media for DSM system 10. Library server process 16 issues media movement commands to automated libraries 32, and interfaces to operator consoles for manual media operations, i.e., shelf management.

Volume server process 18 handles mounted volumes, issuing drive-related commands, such as locking drives 34 and assigning drives to processes. Volume server process 18 also sets up DSM data movers 20 that are configured to read and write DSM media volumes, and to communicate with other client data movers 21 and DSM data movers 20.

A data mover process 20, 21 is instantiated at each data endpoint. DSM client library 12 sets up client data movers 21 to communicate with the user application or the user file system 30. The volume server 18 sets up DSM data movers 20 to read and write DSM volumes. The basic functions of the data movers 20, 21 are (1) receive instructions from the DSM server 14 to begin a data transfer, and return status; (2) read from or write to a data endpoint, e.g., a DSM device, or user file/user stream 30; and (3) transfer data to, or receive data from, another (possibly remote) data mover.

A DSM agent 22 is a privileged client application that is tightly integrated into DSM system 10. DSM agents 22 help enforce policies that are set up by the DSM administrator 24. Examples of operations performed by DSM agents 22 are (a) migrate files from one DSM Store to another; for example, an agent may move files from a RAID disk to a magneto-optical (MO) drive and/or to a tape based on the time of their last reference; (b) delete files that have reached a certain age; (c) compress tape volumes by removing stale files (files that have been deleted by an application); (d) retension tapes; (e) copy and remove aged media; (f) copy or move files to remote DSM system(s); (g) import volumes from a foreign system; and (h) transfer a Store to a different (perhaps more modern) media type.

DSM administrator applications 24 are privileged applications used to configure, monitor, and manage the DSM system 10. In particular, DSM administrator applications 24 allow setting of migration policy and security levels. Administrator applications 24 are written using the privileged DSM administrator API functions. Database server 26 stores information vital to the operation of DSM system 10. The database server 26 provides secure, robust, transaction-oriented storage and efficient search and retrieval mechanisms.

DSM client library 12 provides the client-side implementation of the DSM Client API. The DSM Client API functions are presented to client applications as "C" functions. Internally, the functions are implemented in C++, and a C++ object interface could also be available to client applications. The client library is thread-safe, allowing for concurrent multi-threaded user applications. A user application thread can have multiple DSM connections, and there may be multiple DSM files open on each connection. The library maintains state for each connection and each open file.

All Client API functions can be made synchronous. Certain functions, such as file reloads (DSMReloadFile), can either schedule a task, or wait for the task to complete. In either case, the function returns as soon as the operation it requests (the scheduling or the task) is complete. In a preferred embodiment, there are no asynchronous mechanisms such as callbacks, waits, or event notifications. For scheduled tasks, there are no specific API functions to find out if the task is completed, although the application can be configured to determine if the task is complete by examining the state of the File or Store involved.

Most of the Client API functions preferably can be translated directly into DSM server function calls and processed entirely in the user thread space. The following functions can be provided to establish a data connection, and create a separate data mover thread to handle the movement of the data between the client file or stream 30 and the DSM device 31: (1) DsmCreateFile; (2) DsmOpenFile; (3) DsmStoreFile; (4) DsmRetrieveFile; and (5) DsmReplaceFile. Data mover threads are used by DsmReadFile and DsmWriteFile functions. Threads created by DsmCreateFile and DsmOpenFile are destroyed by DsmCloseFile. Threads created by DsmStoreFile, DsmRetrieveFile, and DsmReplaceFile are destroyed at the completion of the operation.

Figure 2:
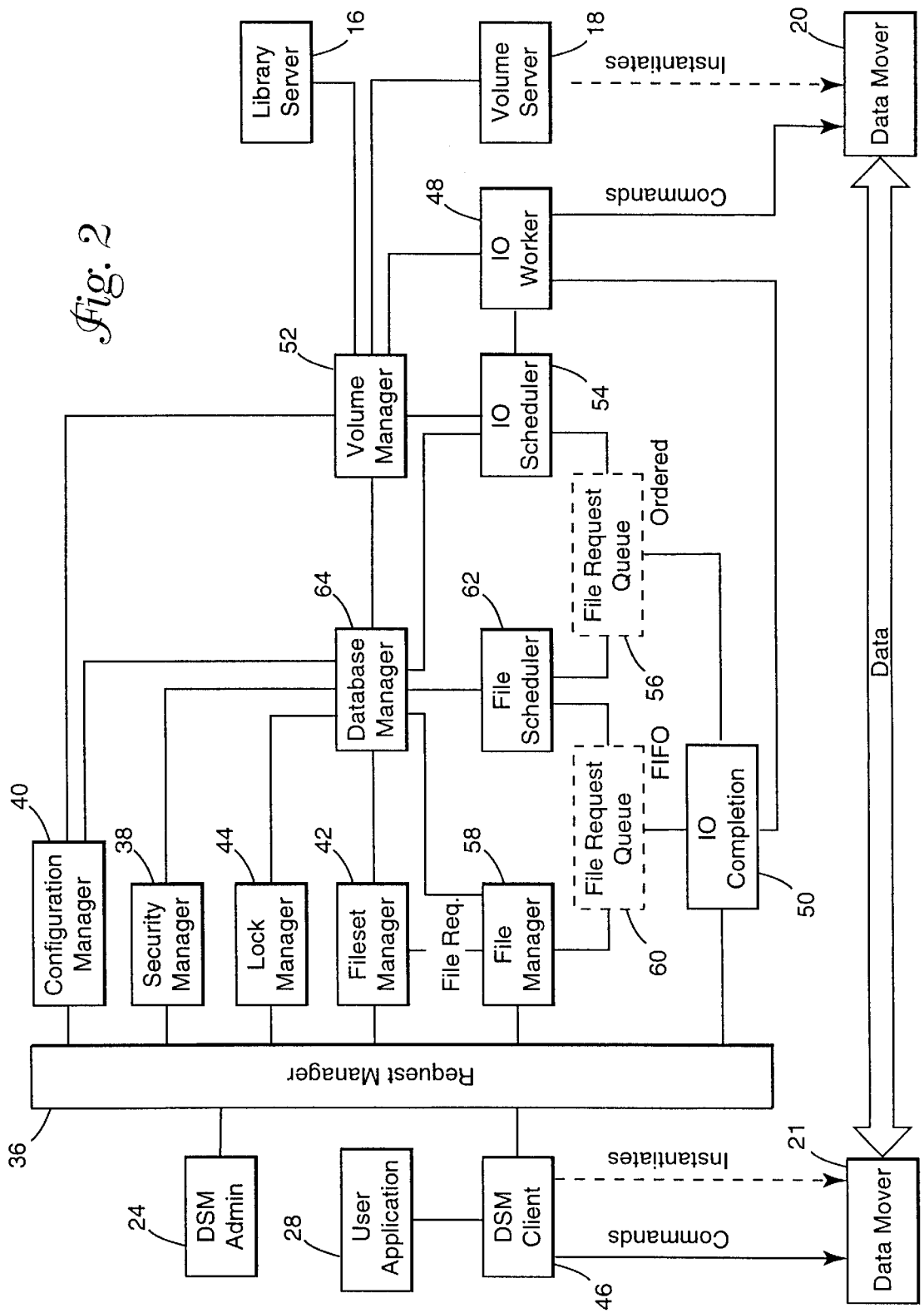
FIG. 2 is a functional block diagram of server component in a system as shown in FIG. 1.

FIG. 2 shows the major components of an exemplary DSM server 14 forming part of system 10 as shown in FIG. 1. In particular, FIG. 2 illustrates the relationships of the DSM server components to other components of DSM system 10. The bold boxes in FIG. 2 denote DSM server components. The first DSM server component to be described is request manager 36. Request manager 36 provides a network connection point for client and administrator applications. The DSM server 14 preferably is multi-threaded, and request manager 36 dispatches incoming requests to appropriate threads so that it can handle other new requests. The various components of DSM server 14 will be described in greater detail below.

With reference to FIG. 2, request manager 36 routes incoming requests based on the type of request. Requests that do not deal with specific files and filesets are handled by security manager 38. These requests include Connection API requests, e.g., Logon, and Security API requests. Requests that change the DSM configuration are handled by configuration manager 40. These requests include all requests that modify the physical configuration (Libraries, and Media), and those that modify the logical configuration (Stores, Volumes, and Remote Servers). Fileset requests are handled by fileset manager 42. Each Fileset denotes a group of associated files. Fileset manager 42 decomposes Fileset requests into multiple File requests and passes them off to file manager 44. Requests that process individual files are handled by File manager 42, Requests for explicit file locks, i.e., a locking down of files onto a particular volume, are handled by lock manager 44. When an input/output operation (IO) is completed by a DSM client 46 or an 10 worker 48, IO completion function 50 is dispatched.

Reference will now be made to security management features of system 10. Security manager 38 interfaces to a DSM security database, and is responsible for establishing logon sessions and maintaining all session information. The tasks handled by security manager 38 include (1) connection management; (2) user administration; (3) file permissions; and (4) store permissions. The connection management task handles logon attempts, validates username and password, and issues a security token to the requesting application (via the client library). Also, the connection management task validates the security token on all other requests. The user administration task handles all maintenance of Users, Groups, and passwords. The file permissions task maintains and validates Users and Group permissions for accessing Files. The store permissions task maintains and validates Users and Group permissions for accessing Stores. Security manager 38 also maintains session-level locking information.

As an example, DSM system 10 may implement a security model having the following characteristics: (1) privileges; (2) DSM Users; and (3) Groups of Users. Privileges include Create, Read, Write (where Write implies overwrite and delete). For every DSM User, a Logon and a Password are assigned. For Groups of Users, (a) every User is a member of one or more Groups; (b) every User has a Default Group of which he is a member, (c) for each session, the User is assigned an Active Group for that session, and Files created during that session are associated with the creator's Active Group; (d) at logon, the Active Group for the User is set equal to the User's Default group; (e) every Group has a DefaultStoreID; (f) the administrator creates Users and Groups, assigns Users to Groups, and sets the User's Default Group; (g) every file has one Owner and one Group; (h) every file has separate read and write permissions for the owner, for the group associated with the file, and for others; and (i) every Store has a set of Create, Read, and Write permissions for each group or user that can directly access the files in that Store. The Active Group can be changed by the User through the API to any group of which the User is a member and remains in effect for that session or until the User changes it again.

If a User creates a new file without specifying a StoreID, the new file is created using the DefaultStoreID associated with the User's current Active Group. The User can change his Default Group, but cannot change the groups to which he belongs. By default, the Owner of a file is the user who creates the file and the Group is the owner's Active Group when the file is created. By default, the owner has read and write permissions, the group has read permissions, and others have neither. This default can be changed by the administrator, while file permissions can be set and changed by the owner and administrators. Finally, store permissions are set by the administrator.

Note that permissions only need to be set for Stores that the Administrator allows users to access directly, typically Initial Stores only. Other stores connected through policies do not need user or group permissions unless users require direct access to those Stores. The Collections of Stores may have the following characteristics: (i) Every Store belongs to zero or more collections; (ii) User and group permissions may be changed on a Collection basis; and (iii) Collections are strictly an administrative convenience. Permissions are always stored on a Store basis, and never on a Collection basis.

When a user connects to DSM system 10, the DSM system verifies that the UserId and Password are known. When a user performs a function, DSM system 10 determines which Store, file, and operation (create, read, or write) is involved. There may be two files, and the files may be in the same or different Stores. Each file may have a different operation. For each file, DSM system 10 will: (1) verify that the user or some group the user belongs to has permission to perform that operation in the Store; and (2) verify that the user has permission to perform that operation. Verification of user permission proceeds as follows: (i) if the user is the owner, compare operation with owner permissions, (ii) else if the user is a member of the file group, then compare operation with group permissions, (iii) else compare operation with other users' permission. The Store permissions need only be checked against the Store specified in the user command. If the file is actually stored to or fetched from another Store, the permissions for the Store used are not checked. No security check is made on DSM system-initiated operations.

The following tables are exemplary of those associated with the security model within DSM system 10:

Users Table:

| | |
|---|---|
| UserID | Numeric GUID assigned to the user |
| Logon | The user's logon used to connect to DSM |

-continued

| | |
|---|---|
| Password | The (encrypted) password used to connect to DSM |
| DefaultGroupID | The ID of the user's default group |

Groups Table:

| | |
|---|---|
| GroupID | GUID assigned to the group |
| GroupName | The name of the group |
| DefaultStoreID | New files will be created in this Store if the user does not specify a StoreID, where the GroupID is the User's ActiveGroupID. |

GroupMember Table (Primary key on UserID and GroupID fields):

| | |
|---|---|
| UserID | The user who is part of the group |
| GroupID | A group the user is part of |

File Table (only security-related attributes are listed):

| | |
|---|---|
| FileID | The GUID for this file |
| OwnerID | The UserID of the owner of the file |
| GroupID | The GroupID of the group the file is associated with |
| Permissions | The read/write permissions for owner/group/other |

Store Table (only security-related attributes are listed):

| | |
|---|---|
| StoreID | The GUID for this Store |
| DefaultPerm | Default owner/group/other permissions for new files created in this Store. |

StoreAccess Table (indexes on StoreID and on AccessID):

| | |
|---|---|
| StoreID | The Store ID |
| AccessID | A GroupID or UserID that has access to this Store. |
| Permissions | The encoded create/read/write permissions for this user or group in this Store. |

Collection Table

| | |
|---|---|
| CollectionID | The GUID for this collection |
| CollectionName | Name for this collection |

CollectionMemberTable

| | |
|---|---|
| CollectionID | A collection a Store belongs to |
| StoreID | The Store that is a member of the collection |

When a user connects to DSM system 10, his Logon and Password are verified, and his ActiveGroupID is set to the User's DefaultGroupID. The Stores that the user can access and the permissions for those Stores are obtained once from the GroupMember and StoreAccess tables and cached by DSM system 10 for the open connections. The number of Stores is typically small, but it could be relatively expensive to check if the user is a member of a number of groups. Once this information is cached, checking Store permissions during this session is trivial. If permissions change while the user is active, the cached permissions become invalid and need to be regenerated.

The cached permissions list for the user contains any Stores for which the user has specific permissions, and Stores for which any group that the user belongs to has permission. User permissions will override all group permissions. Multiple group permissions will be cumulative. That is, if there is a permission record for the individual user for a Store in the StoreAccess table, then records for that Store for any groups to which the user belongs are ignored. If there is no record for the user, then his permissions in a given Store will be the sum of permissions for the groups to which he belongs within that Store.

File permission for a user can be checked as follows: (1) the logged on user's UserID is checked against the file OwnerID; if they match, the file Owner permissions are used; (2) otherwise, for each group to which the user belongs (from the GroupMember table), the GroupID is checked against the file's GroupID and, if a match if found, the file Group permissions are used; (3) otherwise, the file Other permissions are used. This algorithm is easily encoded in a stored procedure and executed by the database engine.

The above security implementation provides a number of advantages. For example, it is easy to implement basic security, but possible to implement detailed security. Also, this security implementation requires very low overhead for sites that have relaxed security requirements, or implement security using native OS facilities. The ability to secure individual files is also provided, along with the ability to restrict or enable individual users because user privileges override group privileges. Multiple-group membership makes it easy to add access to Stores and groups of Stores (collections) for individual users or groups of users. Further, temporary groups with limited access are easily created and removed. Finally, store permissions allow sites to basically ignore file privileges (enable all permissions for all users) and control access by Store only.

Configuration Manager 40 interfaces to a Configuration Database, and handles all requests that modify the configuration. These include all requests that add, delete, or modify parameters of the following entities: (1) sites and DSM services; (2) racks and shelves; (3) libraries, drives, pickers, slots, and ports; and (4) Media and Volumes. Configuration manager 40 interfaces with volume manager 52 and with IO Scheduler 54 for media-related and volume-related requests. For example, a request to format a volume will build an IO Request and add it to the IO Request Queue 56. IO scheduler 54 will handle the request when a drive becomes available, and volume manager 52 will issue the appropriate requests to the library server 16 to mount the volume, and to the Volume Server 18 to format the volume.

Fileset Manager 42 handles requests that deal with all files in a Fileset. Fileset manager 42 translates the Fileset request into a set of File requests for the file manager, tracks the completion of the associated File requests, and notifies the requestor when the Fileset operation is complete.

File manager 58 translates client requests and fileset manager requests into FileRequest objects and places them on the FileRequest Queue 60. File manager 58 tracks the completion of File requests and notifies the requester when a file operation completes.

File scheduler 62 sequences requests for a given file when necessary. Logically, File scheduler 62 maintains a First-In-First-Out (FIFO) queue of requests for each file. A new request to read a file can be started if there are no write requests for that file ahead of it in the queue. A write request for a file can be started only if there are no other requests ahead of it in the queue.

When File scheduler 62 determines that a file request can be started, it creates one or more IO Requests and places them on the IORequest Queue 56. The file request remains in the FileRequest Queue 60 until it is complete, so that file manager 58 can identify conflicts that might delay the start of new requests for the same file.

A DSM file may be split into multiple chunks on one or more physical volumes. Furthermore, if both the source and destination of a file operation are on DSM media, the source and destination may have an unequal number of chunks and the chunks may be of unequal size. File Scheduler 62 converts a File Request into one or more segment IO requests, where each segment is of equal size on the source and destination volumes.

Note that a new volume may need to be mounted for the source or destination or both at each segment boundary. File Scheduler 62 generates an IO Request for each segment, which includes information about the volumes that are required to satisfy the request. The IO Requests are placed on the IO Request Queue 56 for IO Scheduler 54.

For the destination of a write or copy request, only the destination Store may be known.

Selecting the volume within the Store may be postponed until a drive is available to service the request. The task of selecting a volume is given to the IO Scheduler 54. The role of the IO Scheduler 54 is to select the next IO Request to be processed. IO Scheduler 54 selects requests from the IO Request Queue 46 in order to maximize the utilization and throughput of available devices, while guaranteeing some level of service to all clients. File conflicts are resolved by File Manager 58, so the IO Scheduler 54 has a great deal of freedom in reordering IO requests. When an IO request finishes using a drive, the algorithm for selecting the next request to process takes the following into account: (1) high-priority requests that can use the drive; (2) other requests that can use the volume that is in the drive; (3) requests that can use a different volume in the same library; and (4) for sequential devices, such as tapes, the file segment position on the media relative to the current media position. A request may have originated as a high-priority request, or may have had its priority elevated based on the length of time it has been queued. Other requests that can use the volume that is in the drive may include requests that do not specify a specific destination volume, and for which there is room on the volume in the drive.

The select request is passed off to an IO worker thread 48. An IO worker thread 48 is dispatched to handle IO requests, especially those that may take some time. IO requests include Issue Volume requests to the Volume Manager 52. When an IO request is selected, the IO Scheduler requests the necessary Volumes from the Volume Manager 52 and handles the response. The Volume Manager 52 will see that the volumes are mounted and the Data Movers 20, 21 are ready. For data transfers that involve two DSM endpoints (as opposed to one client endpoint and one DSM endpoint), an IO Worker 48 is dispatched to direct the data transfer. When both the source and destination Data Movers 20, 21 are in place, the IO Worker 48 issues the command to the appropriate Data Mover to initiate the data transfer.

When a data transfer is complete, the IO Completion 50 functions handle the completion. It updates the status of the request on the IO Request Queue 56. If an IO completes abnormally, such as when the destination device runs out of space, the IO Completion routine 50 may create new IO requests to complete the IO operation. When all IO requests associated with a file request are complete, the file manager 58 is notified.

Volume Manager 52 carries out the following tasks: (1) maintains the records in the Volume and Store tables in the database; (2) aids in selecting appropriate destination volumes for IO Requests; (3) gets volumes ready for transferring data; and (4) when data transfer is complete, releases the volumes. In preparing volumes for transfer, volume manager 52: (a) issues Volume Mount requests to the Library Server 16 and handle the responses; and (b) issues requests to Volume Server 18 to prepare the drive and volume for file segment commands, and handle the responses. Volume Server 18 sets up Data Mover 20, 21. To release the volumes, Volume Manager 52 issues requests to Volume Server 18 to release the volume and drive, and issues requests to Library Server 16 to unmount the Volume.

Database Manager 64 provides a programming interface to the DSM database that is independent of the underlying database implementation. A Library Server process 16 executes on each host that manages removable media for DSM system 10. Library Server process 16 issues media movement commands to automated libraries, and interfaces to operator consoles for manual media operations such as shelf management. The commands that Volume Manager 18 issues to Library Server 16 for normal operations are independent of the type of library involved. Library Server 16 translates the Mount and Unmount commands into specific device commands that control pickers in automated libraries, and/or into operator commands for manual libraries and shelf management of automated libraries.

A Library Server 16 has a well-known port address on which the DSM Server 14 can communicate. A Library Server 16 will spawn multiple threads to allow concurrent operation of multiple pickers. For the cases where the Volumes in a Store are not on removable media, the Library Server function may not be necessary, or may be located on the DSM Server host even if the media resides remotely.

Volume Server process 18 executes on each host having drives that handle DSM volumes. The roles of the Volume Server 18 are to: (1) issue device-oriented commands such as mount the file system and lock a volume in a drive; (2) perform volume-oriented commands such as (a) partition and format a volume, (b) read and write the volume label, (c) return volume statistics from the operating system, such as total space, space used, and space available, (d) enumerate files on a volume, and (e) perform I/O control such as rewind or position; and (3) set up a Data Mover 20, 21 for each concurrent file-related operation. For random-access devices that allow concurrent operations, such as hard disk and MO, a Data Mover would be established for each concurrent operation.

There is one Volume Server process 18 per host that controls DSM drives. The Volume Server 18 has a well-known port that the DSM Server 14 can use to issue commands. The Volume Server 18 is implemented as multiple processes or threads. The DSM Data Mover 20, 21 objects spawned by the Volume Server 18 may be implemented as threads of the Volume Server process.

Data movers 20, 21 can be instantiated in two places: (1) on client hosts by the DSM client library 12 to read and write user files and streams; and (2) on hosts that have DSM drives by the Volume Server 18 to read and write DSM volumes. A Data Mover process 20, 21 has two communication ports that are made known to the DSM Server 14,. One port is used by the IO Scheduler 54 to issue instructions for file-related operations. Common commands include: (a) create a file; (b) delete a file; (c) return information about a file (metadata); (d) Read a file or portion of a file from media and transfer it to another Data Mover; (e) prepare to accept a file or portion of a file from another Data Mover and write it to media. The other port is used to transfer data from one Data Mover 20, 21 to another data mover. Data transfer operations always involve two Data Mover process 20, 21, and the two processes are each made aware of the communications link. The implementation may have two connections between Data Movers, one for commands and one for data.

DSM Agents 22 are processes that typically run on the same host as the DSM Server 14, and work with the DSM server to implement policies set up by the Administrator 24. One or more DSM Agents 22 may be responsible for the following types of tasks: (a) migrate files from one DSM Store to another, e.g., from a RAID disk to a magneto-optical (MO) drive and/or to a tape drive based on the time of last reference to the file; (b) delete files that have reached a certain age; (c) compress tape volumes by removing stale files (files that have been deleted by a user application); (d) retention tapes; (e) copy and remove aged media; (f) copy of move files to remote DSM system(s); (g) import volumes from a foreign system; and (h) transfer a Store to a different (perhaps more modern or up-to-date) media type. DSM agents are privileged client applications that use the Client API and the DSM Administrator API.

Database Server 26 stores information vital to the operation of DSM system 10. Database Server 26 provides secure, robust, transaction-oriented storage and efficient search and retrieval mechanisms. The information maintained by the Database Server 26 may include: (a) the DSM security database containing user IDs, passwords, and privileges; (b) physical configuration, including local and remote libraries and drives, and external media storage; (c) remote DSM servers and their communication parameters; (d) media inventory, including the location of each piece of media, and the space available; (e) file metadata, including the security attributes and media locations of each file; (f) logical grouping of media into DSM Stores, and information about each Store; and (g) policy parameters used by the DSM server and DSM agents. The database can be stored in tables and the database implementation provides a relational view of the data.

Having described the architecture of DSM system 10, reference will now be made to the policy algorithms implemented by the system. Policies can be placed in the following categories: (1) policies dealing with maintaining copies in stores; (2) policies dealing with media and volumes; and (3) miscellaneous policies. Policies dealing with maintaining copies in stores may include (a) an initial store policy that specifies the default store(s) into which a new file is placed; (b) a maximum file size to store, which may be bypassed for larger files, in lieu of an alternative store; and (c) an alternate store to use if the file size exceeds the maximum specified.

A migration policy may (a) enable migration, in which case lowest level stores would not enable migration; (b) specify migration low and high watermarks; (c) specify the store to which files should be copied when the present store reaches some capacity threshold; (d) specify migration ranking criteria, such as oldest, least recently used, size, combination of age and size, (e) specify use of fileset migration, and allow the user to choose different levels of adherence to this policy; and (f) set a migration time window, i.e., a period of time in which to carry out the migration.

A deletion policy may (a) enable automatic deletion, which typically would not be enabled for lowest level store; (b) specify stores on which copies must exist before a file is deleted from this store; (c) specify deletion from the original store immediately upon migration to the new store; (d) set a suggested minimum age at which to delete a file; (e) set a suggested maximum age at which to delete a file, in which case the file may be deleted even if space is not needed; (f) specify marking of deleted files as obsolete without deletion, enabling recovery of a deleted file; (g) specify marking of overwritten files as obsolete without deletion, enabling recovery of any version of a file; (h) set a maximum time to retain an obsolete file beyond deletion (obsolescence); and (i) set a maximum time to retain any file beyond last reference. A reload policy may (a) require reloading of an entire fileset when a file is reloaded; and (b) specify a maximum total size of files in a fileset to reload.

Among the policies dealing with media and volumes, a chunking policy may: (a) allow chunking files on the given store although some users may choose to disallow splitting of files across volumes; in this case, files larger than the size of one volume would be rejected; and (b) set a minimum chunk size to prevent a proliferation of small chunks, which may not apply to a final chunk. A volume selection policy may specify that the selected volume will be (a) the first available; (b) the best fit in terms of storage space or other characteristics; (c) the most recently written to keep files in more or less chronologically ordered on media; (d) the least recently used to keep volumes cycled through drives and spread new files across media for concurrent retrieval; (e) a round robin format in which volumes are cycled through the drives; and (f) with the most current file in the same fileset or any file in the fileset.

A drive selection policy may specify that files be stored (a) on a drive that is the first available; or (b) to balance usage among drives. A shelf management policy may (a) enable shelf management for the given store although shelf management for intermediate stores may not be desired; (b) use Free Store from which new volumes can be drawn; (c) set a tape retention interval; (d) set a maximum media age according to which the system will copy to new media and scrap old media when the age is exceeded; (e) set a maximum mount count by which the system will copy to new media and scrap old media when the count is exceeded; (f) set a tape compaction threshold specifying the minimum bytes to try to recover; (g) specify merging files in a fileset onto media or, alternatively, only upon migration; (h) set a shelf management time interval that specifies a best time to compact and retention tapes and merge filesets; and (i) specify import/export volumes and notify caller when an offline file is accessed.

An inventory policy may provide that the library be periodically inventoried, inventoried using a barcode inventory method, or using a volume label inventory method where each volume is loaded. A number of miscellaneous policies may be employed including a logging policy whereby the system logs, e.g., deletions, overwrites, stores, and retrievals.

To implement the various policy categories described above, DSM system 10 makes use of a set of policy algorithms. When DSM system 10 receives a new store-file request from an Endpoint Client, for example, it will store the file in the Store specified in the request if one is specified. If no Store is specified, DSM chooses the Default Store for the User's Active Group. Typically, this will be a direct-access storage device, such as a RAID disk. In any case, exactly one Store is chosen. Whenever the size of the file to be stored exceeds the non-zero FileBypassSize attribute of the selected store, then the store specified in the FileBypassStore attribute is selected instead. If no store is selected because the file size exceeds all non-zero FileBypassSize values, then the store fails, it is logged, and the requester is notified.

When a Store is selected, file manager 58 creates a new File object in the Store and schedules a file copy from the Client Endpoint to the Store. Whenever a copy is scheduled, the destination Store is added to the File's vsScheduled attribute. Whenever a copy completes, the destination Store is removed from vsScheduled and added to vsResidence for that file. Also, when a copy completes, the File's vsHeld is updated to indicate whether or not this file is a candidate for deletion (primarily whether it has been migrated), and the Store's BytesHeld property is updated accordingly. Since a new file typically cannot be deleted until it is migrated, the Initial Store is usually added to vsHeld following the store, and the file size is added to BytesHeld.

If a maximum lifetime is specified for the file, it is placed in the file's Lifetime attribute. If none is specified, then the MaxLifetime attribute of the Store is placed in the file's Lifetime attribute. Whenever a copy to a Store completes, DSM will look at a vsCopyTo indicator for that store, and immediately schedule copies from this Store to all the Stores specified if copies do not already exist or are not already scheduled. This is essentially the same as an immediate migration from the Initial Store to the Stores in the vsCopyTo.

Overwriting a file is equivalent to deleting the file and storing a new file but reusing the old FileID. A file is deleted by giving the file a new FileID and then scheduling the deletion using the new FileID. The act of physically deleting the file can be queued. Once the file is given a new FileID, other requests using the old FileID, such as an overwrite request, can proceed ahead of the delete. Since copies of the file may exist on a number of different stores, deleting the file may require mounting one or more volumes, which could take some time. A client desiring to overwrite the file will not have to wait for the previous copy to be physically deleted in order to write the new copy. Overwriting a file requires that the File be Locked.

A Delete File request is always the last request allowed for a file. When a Delete File request is received, the file is marked for deletion. If a RetainDeleted property is set for the Store, then the file is flagged as Obsolete; otherwise the file is flagged as Deleted. All subsequent requests for that file, except those dealing with deleted files or versions, will return a status indicating that the file does not exist. The Delete File request is processed by copying the FileID property into an OrigFileID property, and then giving the file a new unique FileID. In doing so, DSM server 14 can process the Delete File request as it would a normal file, while retaining the information needed to undo the delete if the configuration allows it. Furthermore, this supports multiple deleted (obsolete) file versions, while maintaining a unique FileID for every unique file version in the system.

Once a new FileID has been assigned to a file, deleting the file from DSM is equivalent to deleting it from all stores in which it is resident, which can be determined from a vsResidence vector. The file record is then deleted if a bRetainDeleted property is not enabled for this store. Once a new FileID has been assigned to the file, the act of physically deleting the file can be queued, and other requests for the same FileID, such as an overwrite request, can proceed ahead of it. Because copies of the file may exist on a number of different stores, deleting the file may require mounting one or more volumes, which could take some time. A client wanting to overwrite the file will not have to wait for the previous copy to be physically deleted in order to write the new copy. The file must be Locked in order to be deleted.

Deleting a file from a Store is not the same as deleting a file from DSM system 10. The file may be deleted from one Store and still exist in other Stores. A file is deleted from a Store as part of the migration scenario. Deletion is a scheduled task, since it may involve mounting one or more volumes. In most cases, it is a higher priority task than writing to the volume, so that the space freed by the deletion will become available sooner. For most types of media that support deletion. as opposed to marking a file as stale, the delete operation is very fast once the volume is mounted.

To delete a copy of a file from a store, the following steps occur: (a) the store is removed from a vsResidence vector for the file; consequently, future read requests for this file on this Store will find the file is not resident, even if the physical deletion has not yet occurred; (b) the Store is added to the file's vsDeleting vector; (c) a FileSegmenter process is invoked to delete the individual file chunks; (d) the FileSegmenter process schedules the deletion of the individual chunk, and the number of bytes in each chunk is subtracted from a BytesRemovable or BytesHeld property and is added to a BytesDeleting property of the volume and store. An IOScheduler process handles deleting the chunks. As the physical deletion occurs, the size of the chunk is subtracted from the BytesDeleting property and added to the BytesFree property of the volume and store. When all chunks are deleted, the Store is removed from a vsDeleting property for the file.

If a copy of a File into a Store is requested, e.g., a Reload, while the file is being deleted from the Store, the deletion must complete before the copy begins. Otherwise, multiple copies of the file would exist in the same Store, which may be difficult to support. Note that this does not apply to Overwriting a file because the FileID of the old copy is changed prior to the Overwrite operation. No file lock is required to delete a File from a Store.

Copying a file is one of the more important operations in DSM. It generally would be used in all the following situations: (a) to place files into DSM system 10 by doing a copy from a Client Endpoint to a Store; (b) to return files to a client, by doing a copy from a Store to a Client Endpoint; (c) to migrate a file from one store to another; (d) to reload a file into the cache store; (d) compacting media; (e) aging media; and (f) migrating to new media types.

File copy requests are handled by a FileSegmenter process. The actions described below take place in response to a file copy request. The element corresponding to the source Store is incremented in the vsSourcing property for the file. The destination Store is added to a vsScheduled vector for the file. The FileSegmenter process is called to generate IO Requests to perform the copy. Volume Manager 52 will select one or more destination volumes and reserve space by incrementing BytesReserved and decrementing BytesFree. IO Scheduler 54 and Data Mover 20, 21 will copy the bytes. A BytesReserved property will be decremented and a BytesHeld or BytesRemovable property will be incremented for both the destination volume(s) and the destination Store. If the file is held, the vsHeld bit for the destination store will be set in a File.vsHeld vector.

When the copy is complete, the destination Store will be removed from the file's vsScheduled property and added to a vsResidence property for the destination file. The source is evaluated to see if the file is a candidate for deletion and the File's vsHeld vector is updated accordingly. Whenever a copy to a Store completes, DSM server 14 will look at the vsCopyTo vector for that store, and immediately schedule copies from this Store to all the Stores specified in that vector if copies do not already exist, as determined by the vsResidence, or are not already scheduled., as determined by the vsScheduled vector.

When a client application requests a file from DSM system 10, the following steps take place. First, the store from which the files is to be retrieved must be chosen. The file may exist on multiple Stores. The file vsResidence indicates the Stores in which the file is resident. The Store that is chosen for retrieval will be the Store with the lowest value of a priority property. This will typically be the fastest store. Alternatively, DSM system 10 may determine if a mounted volume contains the file or if a drive is available in a library that contains the file. If the file is not found on the local DSM Server, the Servers in a vhSearch vector for the Store are searched. Second, a copy of the file from the selected Store to the Client application is scheduled. Third, a reload of the file is scheduled if the applicable policy indicates to do so. If the ReloadToStore policy property for the chosen store is not null, and the user request did not specifically suppress reload, then a copy from the chosen Store to the Store specified by the ReloadToStore property is scheduled. Reloads are not scheduled if the Retrieve request specified NO_RELOAD. Reloads are not scheduled if the retrieve is from a remote DSM server, or the file is reloaded to the Store from which that the file was originally requested.

Figure 3:
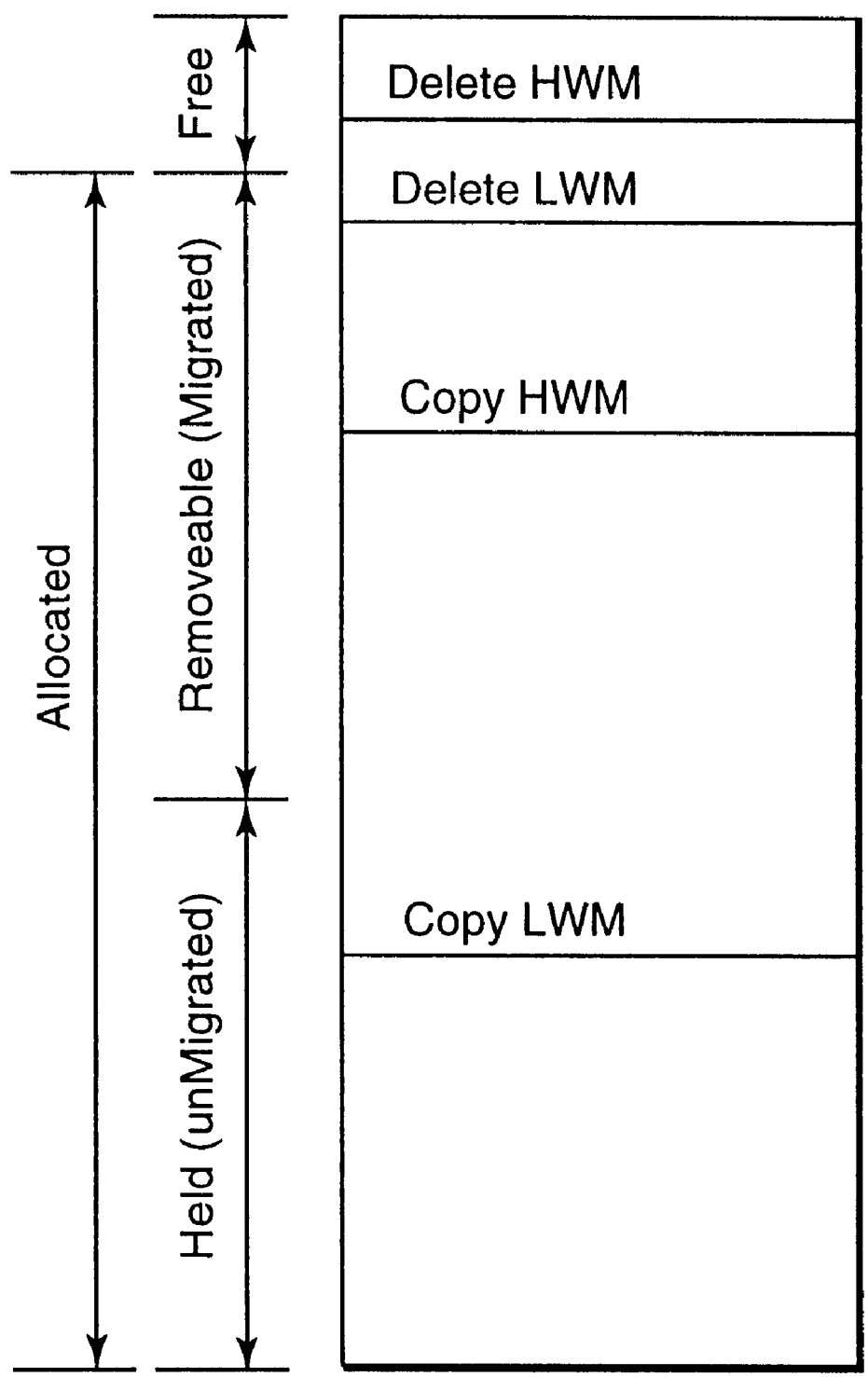
FIG. 3 is a diagram illustrating implementation of migration policy in a system as shown in FIG. 1.

For migration strategies, there are competing goals. First, it is desirable to keep as many files in a Store as possible so that fast retrieval is possible. Second, it is necessary that enough spaced in a Store remain available to handle incoming files. In general, migration is accomplished by performing two operations: (a) copying files from a Store to its Migration store so that a copy is retained; and (b) deleting files from a Store that exist in one or more other Stores. The migration policy has an effect on when these operations are performed. DSM system 10 makes use of four thresholds that control these operations. Copy High-Water Mark (CopyHWM) starts copying to the migration store when the held (unmigrated) bytes exceed this threshold. Copy Low-Water Mark (CopyLWM) stops copying when the held (unmigrated) bytes goes below this threshold. Delete High-Water Mark (DeleteHWM) starts deleting copied files when the allocated bytes goes over this threshold. Delete Low-Water Mark (DeleteLWM) stops deleting when the allocated bytes goes under this threshold FIG. 3 illustrates the concept of watermarks. Bytes that have not been copied to the Migration Store are not eligible to be removed (deleted) from the Store, and are referred to as "Held" bytes. Bytes that have been deleted or never allocated are eligible to be reused, and are referred to as "Free" bytes. The other bytes in the Store that have been allocated and migrated, are "Removable" bytes. The goal of the Migration Agent is to keep the level of allocated bytes between the DeleteHWM and the DeleteLWM so that some Free bytes are always available, and to keep the level of Held bytes between the CopyHWM and the CopyLWM so that some allocated bytes can be quickly converted to Free bytes if needed. The higher-priority task is to keep Free bytes available to be used for files that are being written to the Store by deleting Removable Bytes. However, the Migration Agent cannot delete more Removable Bytes than exist, so it may have to copy files to the Migration Store to make those Held bytes Removable before it can delete them.

Figure 4:
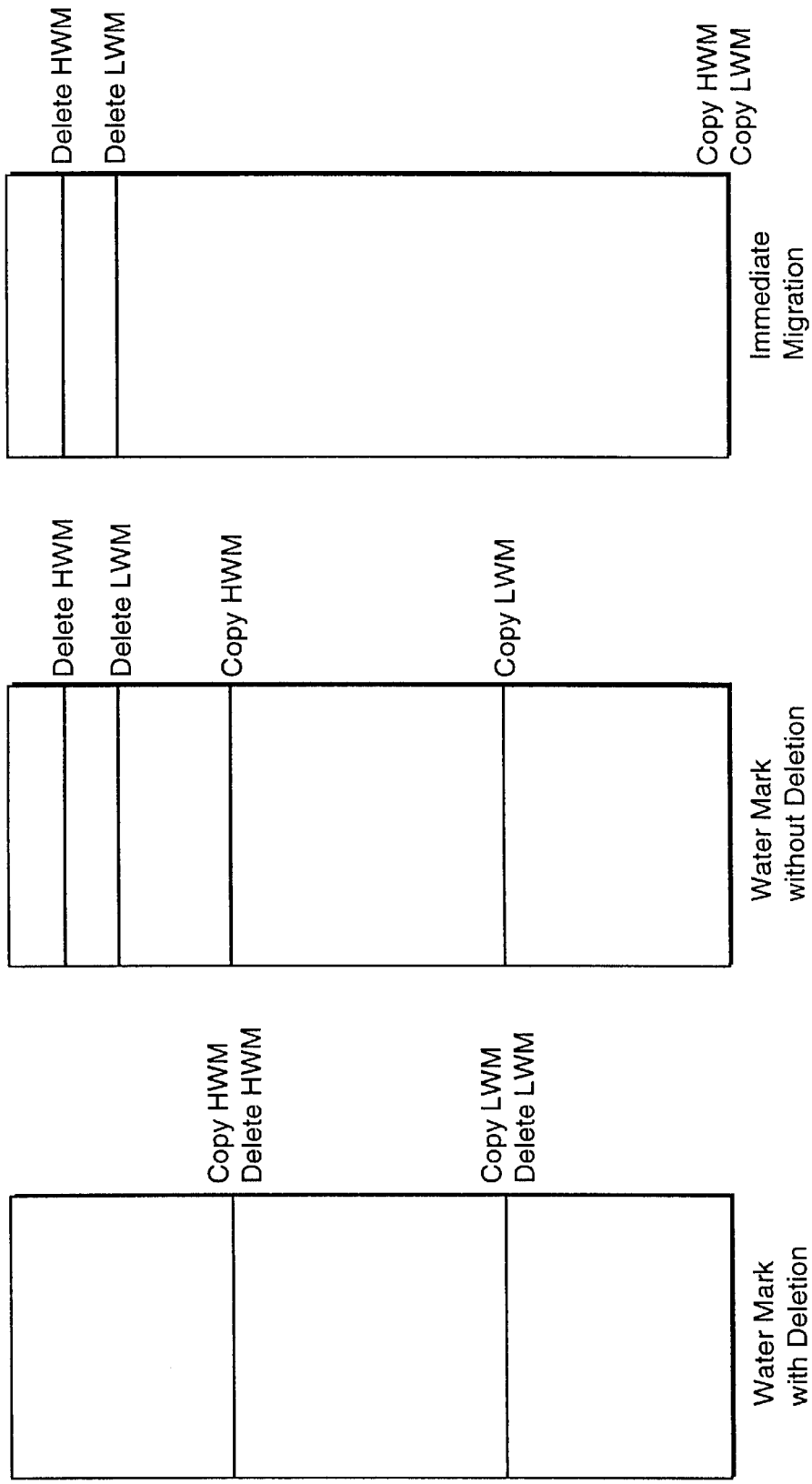
FIG. 4 is a diagram further illustrating implementation migration policy in a system as shown in FIG. 1.

There are at least three migration strategies that are supported by DSM system 10, as illustrated in FIG. 4 and described below. Water Mark Migration with Deletion (Move files from one Store to Another) is a strategy that combines the copy and delete operations. In essence, CopyLWM is equal to DeleteLWM and CopyHWM is equal to DeleteHWM. In this strategy, the migration agent starts to copy files to the Migration Store when the CopyHWM is reached. It copies as many files as necessary to the Migration Store, and deletes them from the current Store, until the CopyLWM is reached. This strategy attempts to always maintain an amount of free space on the Store between the CopyHWM and the CopyLWM. This is the classic water mark migration strategy. The Store can be viewed as a tank of water with a fill pipe and a pump. When the water (incoming files) reaches the High-Water Mark, the pump (the migration agent) turns on and begins emptying the tank. When the water reaches the Low-Water Mark the pump shuts off. During the time the pump is running, water can be entering from the fill pipe. If water is not pumped out faster than it is coming in, the incoming water is backed up or the tank overflows.

One feature of this approach is that migration tends to occur in batches. This can be a positive thing if the batches are such that migration can occur only at non-peak intervals. However, if the High Water Mark is reached during a peak period (which intuitively might happen), then large amounts of migration will compete with peak activity. Furthermore, the migration may become critical in order to keep a Store from filling up. To keep migration at off-peak times, it may be necessary to set the Low and High Water Marks far apart. For example, there may have to be enough room to store the new files for an entire day. Because the Low Water Mark is typically quite low in this strategy, it means that less efficient caching is taking place. The amount of the Store that is being used for caching varies between the DeleteHWM and the DeleteLWM. In this strategy, DeleteLWM is the same as CopyLWM and the amount of caching can go quite low. It may be difficult to determine the best setting for the Water Marks, especially if the workload fluctuates. Furthermore, the water marks may have to be adjusted as the average workload increases or decreases over time.

A variation on the first migration strategy can be referred to as water mark migration without deletion. According to this strategy, files are copied to the Migration Store in the manner described above, but the files are not deleted from the current Store until the space is actually required. In this manner, the DeleteHWM and DeleteLWM are set above the CopyHWM and CopyLWM. This approach is generally acceptable, because once the copy has been made, it generally takes relatively little time to delete the file. In theory, it may be possible to set the Delete water marks at 100% to cause files to be deleted exactly when the space is needed. In practice, deleting is not instantaneous, and in fact may require mounting one or more volumes. Therefore, it may be desirable to keep some amount of space immediately available by deleting files before the space is needed. An advantage of this strategy is that more of the Store is available for caching files. The disadvantage is that some overhead is required to delete the file when the space is needed, and that overhead is not postponed to off-peak times. As with the first strategy, it may be difficult to determine the optimum water marks and they may need periodic adjustment.

A variation of the second migration strategy is to schedule the migration of files as soon as they enter a Store, in essence setting the CopyHWM and CopyLWM to zero. This strategy can be referred to as immediate migration. The advantages are that migration can occur as a continuous low-priority activity, and caching efficiency is optimized as it is in the second strategy. This strategy also has less dependence on the selection of optimal water marks. The disadvantages are that neither copying nor deleting files is postponed to off-peak times, so they may compete with normal activity. However, both may occur as low-priority tasks.

Figure 5:
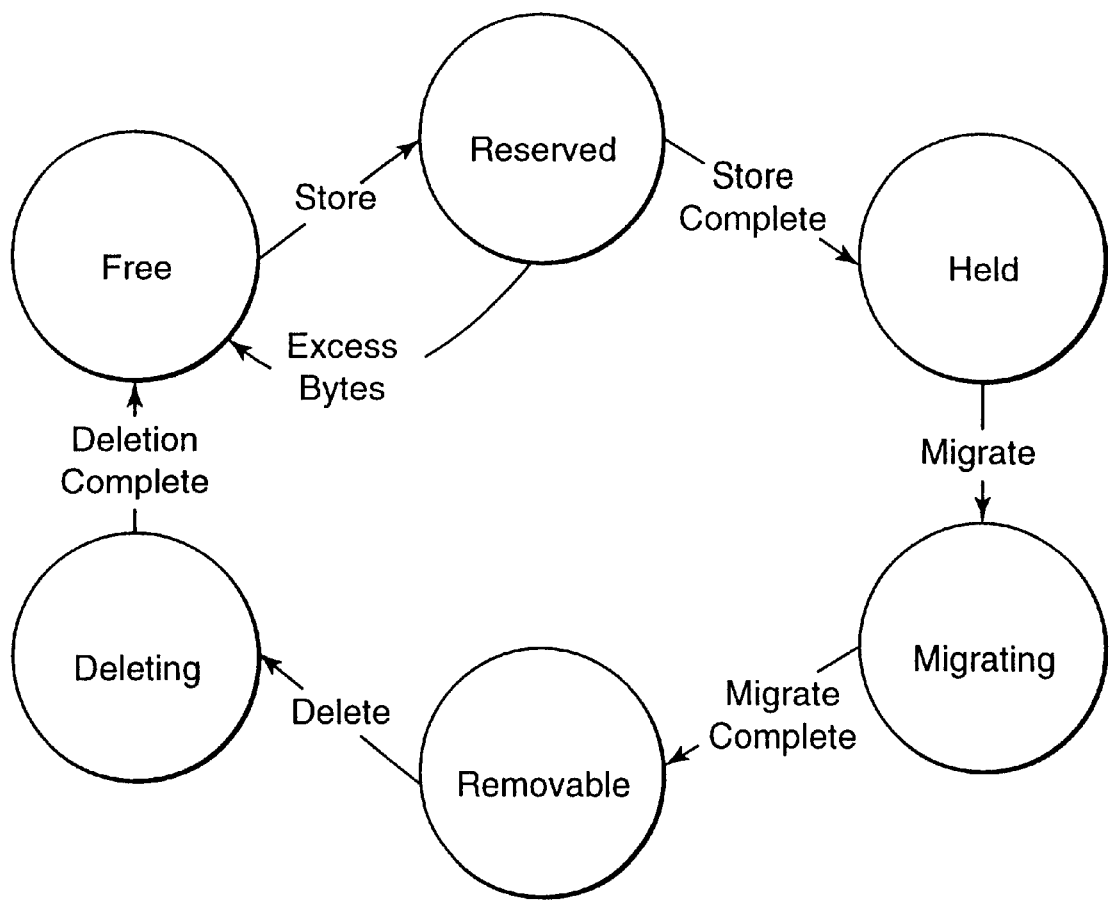
FIG. 5 is a state diagram illustrating state transitions during execution of a migration policy in a system as shown in FIG. 1.
Figure 6:
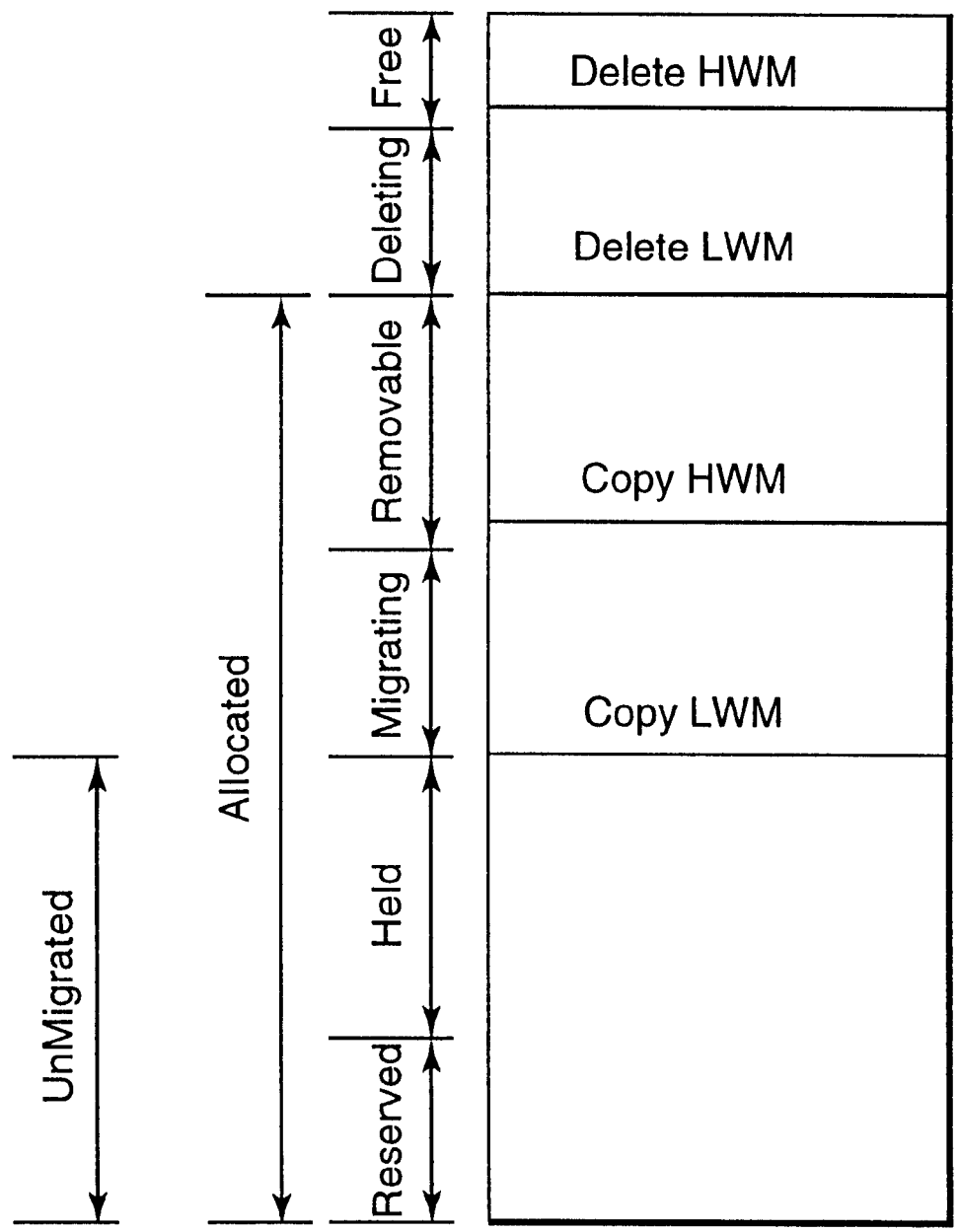
FIG. 6 is a diagram mapping migration states to watermarks in a system as shown in FIG. 1.

In the exemplary embodiment described herein, there are six counts associated with each Volume that indicate the states of the space (bytes) on that volume. The sums of the counts for all the Volumes in the Store are maintained in the Store. The bytes are always in one exactly of the states: Free, Reserved, Held, Migrating, Removable, or Deleting. The common state transitions are shown in FIG. 5 and described below. When a volume is created, all the bytes are in the "Free" state. That is, they are available to be used. When a request is received to store a file, a volume is chosen with enough space to accommodate the estimated file size, and those bytes are moved to the "Reserved" state. When the file is completely stored on the volume, the number of bytes corresponding to the actual file size are typically moved to the "Held" state, indicating that the file must be migrated to another store before it can be deleted from this store. If more bytes were reserved than were actually used, then the excess bytes return to the "Free" state. When a file is selected for migration, the bytes are moved to the "Migrating" state. When a file has been migrated to the next level of storage, it is eligible to be deleted from the current store. The byte count is then moved to the "Removable" state.

When a file is selected to be deleted from a store, its byte count is moved to the "Deleting" state and the delete operation is scheduled. When the deletion is complete, those bytes are moved to the "Free" state. There also may be three long-term states: "Free," "Held," and "Removable." There are also three typically short-term or transitional states: "Reserved," "Migrating," and "Deleting." Other transitions may occur, depending on the migration policy. For example, the policy may define a temporary store, where old files are deleted without ever being migrated. In that case, bytes would transition directly from "Reserved" to "Removable." Another example is when a file is explicitly deleted by a client. In that case, the bytes may transition from "Held" to "Deleting." FIG. 5 completes the picture shown in FIG. 3 by mapping the six states to the watermarks. The specific goal of the migration agent is to keep the number of allocated bytes between the Delete LWM and the Delete HWM, and to keep the number of Unmigrated bytes between the Copy HWM and the Copy LWM.

According to the migration delete algorithm, the Migration Agent monitors the Stores, and when it finds that the level of allocated bytes in a Store is greater than the DeleteHWM, it selects files to be deleted, and schedules them for deletion. The Migration Agent will continue to select files to be deleted until the number of allocated bytes is less than or equal to the DeleteLWM. The Migration Agent does not consider Stores whose DeleteCriteria is DELETE_NEVER. The percentage of bytes allocated is calculated using the following equation.

$$PercentAllocated = \frac{BytesTotal - BytesFree - BytesDeleting}{BytesTotal}$$

The migration agent will select physical files (Chunks) for deletion by age (current time minus the LastAccessTime).

A file is not eligible to be deleted from a Store if any of the following are true: (1) the file is being read from any store (File.ReadCount>0); (2) the files is scheduled to be deleted or written to the stores, as indicated by the File.vsScheduled and File.vsDeleting vectors; (3) the DeleteCriteria of the Store is DELETE_ANY_STORE and the file does not exist on at least one other Store (determined from the vsResidence property); (4) the DeleteCriteria of the Store is DELETE_SPECIFIC_STORE and the file does not exist on all of the Stores specified in the vsDeleteSpecific (determined from the vsResidence property); (5) the Delete-Criteria of the Store is DELETE_MIGRATE_STORE and the file does not exist on the Migration Store (determined from the vsResidence property). The first two of the above conditions will typically not be true for the oldest files on a store. The other conditions will be untrue after the Migration Copy process is complete.

According to the migration copy algorithm, the Migration Agent monitors the stores, and when it finds that the number of percent of unmigrated bytes in a Store is greater than the CopyHWM, it schedules files to be copied to the Migration Store. The steps in migration are as follows: First, it is determined if migration is necessary. Migration will begin if the ratio of unmigrated bytes to the total number of bytes in the Store is greater than CopyHWM, computed by the following formula:

$$PercentUnmigrated = \frac{BytesHeld + BytesReserved}{BytesTotal}$$

If migration is necessary, the Migration Agent will set the Store's bMigrating flag, select files to be migrated (step 2 below), and schedule the migration (step 3 below). As files are selected for migration, the BytesMigrating variable will be incremented and the BytesHeld variable will be decremented. The Migration Agent will continue to select files for migration until the ratio in the equation above is less than the low water mark, CopyLWM. It will then clear the Store's bMigrating flag.

Second, the file to be migrated is selected. A file will be selected for migration from a Store based on the Store migration algorithm. A file is eligible for migration from a Store if: (a) the file is not marked as deleted, where obsolete files are migrated; (b) the file is not being deleted from the present store, i.e., the store is not in the vsDeleting vector; and (c) the file is not already being copied to the migration store, i.e., the Store is not in the vsScheduled vector. When a file is selected for migration, the Migration Agent will add the store to vsScheduled and schedule a copy to the migration Store. If the file is part of a fileset and other files from the same fileset are present in the Store, then those files will be selected next for migration if fileset migration is selected.

Third, a request to copy the file to the migration Store is made if the file does not exist there. The FileSegmenter will add the destination store to the vsScheduled property of the file and handle the physical 10 of the file chunk(s). The BytesMigrating property of the source store will be incremented by the file size, and the BytesHeld will be decremented. The IOScheduler is invoked to handle the physical copy. When the physical 10 is complete, the Store is removed from destination vsScheduled and added to vsResidence for the file. The file size is decremented from the source BytesMigrating. If all of the criterion to release the hold on the file are satisfied, the file size is added to BytesRemovable. Otherwise, the file size is added to BytesHeld.

In reloading a file, a reload request typically causes a file to be copied to the highest-priority Store where the size of the file does not exceed the FileBypassSize of the Store. The source of the copy is the highest-priority Store that contains a copy of the file. Specifically, a reload request can be handled in the following manner: (a) select the reload source; (b) select the Store with the lowest value of the Priority property that contains a copy of the file as determined by the File vsResidence property; (c) if the file is not found locally and there are remote Servers configured, search the remote servers for the file; (d) select the reload destination; (e) select the Store specified by the Reload-ToStore property of the source Store selected in step (a) if the source Store is local, but if ReloadToStore is null, then no reload is performed; (f) if the source store is on a remote server, then select an Initial Store on the local system; (g) if the size of the file to be reloaded exceeds the FileBypassSize of this Store, then select the Store with the next lowest value in its Priority property and continue until a Store is found where the file size does not exceed FileBypassSize; and (h) if the source and destination are the same, no reload is required, otherwise schedule a copy of the file from the source Store to the Destination Store. Normal copy and migration rules apply to reloaded files, including scheduling additional copies per the vsCopyTo. Reloading a fileset is generally equivalent to reloading all the files within the required fileset. All the files will be queued for reloading according to its location if the media type is sequential access.

It is preferable that Migration, CopyTo happen during a time the system is not very busy. For this reason, when criteria for Migration or CopyTo are reached, DSM queues requests so they occur during a preferred time interval. When the high water mark is reached, files will be queued for migration. The actual migration may happen during a preset up time, for example, over night. A maximum number limit will be set by policy for this queue. The migrating queue will not be affected by any action after the file or fileset is already in the Queue. For example, migration policy may be to migrate the least recently used file first. When HWMK is reached, if a least recently used file A is put in the migrating queue before the actual migration takes place, then there comes some kind of request for file A. DSM system 10 will fulfill the requirement and File A now is not least recently used any more but it will be still migrated according to the exiting queue.

The CopyTo function can be queued and the action will be taken in a preferable time interval or according to some other condition. For free store management, a warning can be given when BytesTotal below a given minimum bytes. System should be prepared to add new volumes into FreeStore. Media added to FreeStore must be DSM-compatible media and can be formatted or unformatted. The added media is given a DSM global unique identifier (guid).

The following discussion deals with operations that are performed by DSM agents for shelf management. To facilitate deletion of aged files, each file has a Lifetime property that is set when the file is created. An agent scans the files periodically and deletes any files whose age exceeds their specified lifetime. The age of a file is the difference between the current time and the time the file was last referenced as recorded in the LastReference property. After being deleted, the file is unrecoverable if the Store's bRetainDeleted property is not set. If bRetainDeleted is set, then the file is marked obsolete but can be recovered. If the file is marked obsolete, its LastReference property is set to the time that it was marked as obsolete. The agent also scans for obsolete files and deletes any whose age exceeds the ObsoleteLifetime property of the Store. An agent also scans files in Stores for files whose age exceeds the MaxSaveTime of the Store, and deletes those files from the Stores (migrating when necessary).

For replacement of aged media, each media can specify a MaxAge that sets the age at which media should be copied to new media and discarded. An agent monitors the age of media, i.e., current time minus CreationTime, and instigates the replacement process at the appropriate time. For migration to a new or different media type, the following steps can be used: (a) configure a new Store (NewStore) that is to replace an existing Store (OldStore); (b) configure NewStore to have the same Priority as OldStore; (c) configure the Stores that migrated to OldStore to migrate to NewStore; (d) configure the Stores that sent bypassed files to OldStore to send bypassed files to NewStore; (e) configure NewStore to copy to the Stores to which OldStore copied; (f) configure NewStore to migrate to the stores to which OldStore migrated; (g) configure NewStore to bypass to the store to which OldStore bypassed; (h) configure OldStore to migrate to NewStore; (i) set the ForceMigration flag in the Policy for OldStore. An agent will force the migration of all the files in OldStore to NewStore. Since the new configuration does not store or migrate any files to OldStore, it can be removed once the migration is complete. During the migration, retrievals and reloads of files that are still on OldStore will continue to operate in the usual manner.

To retension media, an agent can be made responsible for periodically checking the LastRetensioned property of the media against the RetensionInterval property of the media type and performing the retension operation at the proper time. For compactable media, typically tapes, an agent will be responsible for periodically comparing the BytesRemovable of a volume against the MinBytesToRecover property of the media type. When BytesRemovable exceeds MinBytesToRecover, a compaction of the media will take place. An agent can be provided to merge oldest files onto volumes for export. When the library capacity reaches some threshold, an agent will combine the oldest files on loaded volumes onto a single volume for export. That volume can then be exported and a fresh volume can be imported.

A number of policy examples are set forth below for purposes of illustration. A first example pertains to a policy that provides for immediate migration. In this example, files that are smaller than the Store 0 FileBypassSize are written to Store 0, and then copied to both Store 1 and Store 2. Files that are larger than the Store 0 FileBypassSize and smaller than Store 1 FileBypassSize are written to Store 1, and then copied to Store 2. Files that are larger than Store 1 FileBypassSize are written to Store 2. Because the copies to the other stores are scheduled right away, there is no need for high water mark migration.

A second example provides for HWM migration and backup. There are three cases of interest in this example. The file is smaller than Store O's FileBypassSize. The file is written to Store 0. When the write is complete, the file is copied to Store 3. When the file ages from Store 0, it migrates to Store 1. Because it already exists on Store 3, it is not copied there again. When it ages from Store 1, it migrates to Store 2. Because it already exists on Store 3, it is not copied there again. The file is larger than the Store 0 FileBypassSize and smaller than the Store 1 FileBypassSize. The file is written to Store 1. After the write is complete, the file is copied to Store 3. When it ages from Store 1, it migrates to Store 2.

Because it already exists on Store 3, the file is not copied there again. The file is larger than Store 0's FileBypassSize and larger than Store 1's FileBypassSize. The file is written to Store 2. After the write is complete, the file is copied to Store 3. Store 2 and Store 3 are both at the lowest level, so vsCopyTo and MigrateToStore would be null. Store 3 is a backup store, so bRetainDeleted and bRetainVersions would be set TRUE. This type of Store is essentially a serial record of everything written to DSM. Any version of any file would be recoverable from this media. This policy can be modified by the ObsoleteLifetime and MaxLifetime properties of the Store.

A third example concerns migration to a new media type. This is similar to the second example, except that a new Store, Store 4, has been added to the system with the intention of migrating all files from Store 1 to Store 4. Note that Store 4 takes the place of Store 1, and Store 1 now just migrates to Store 4. The ForceMigration property would be set in Store 1 to cause all the files in Store 1 to migrate to Store 4 even though they might not otherwise migrate.

The following are several guidelines for practice of the policies described above. If the policy is intended to provide a permanent storage facility, configure a CopyTo from the InitialStore to at least one lowest-level store. If a maximum file size is specified for a Store (FileBypassSize), then a FileBypassStore is configured. The MigrateToStore should usually be the same as the FileBypassStore if there is a FileBypassStore. If a Store (StoreA) specifies a FileBypassStore (StoreB), then StoreB should have the same CopyTo stores StoreA. This ensures that a copy is always done to StoreB.

The FileBypassSize should increase for each level of Store. Each Store related through policy should have a unique value in its Priority attribute. Setting the "bRetainDeleted" property of a Store may be inconsistent with specifying a MaxLifetime for the Store unless an ObsoleteLifetime is also specified. Specifying the MaxLifetime will cause the file to be deleted (presumably to recover the space it used), but "bRetainDeleted" will cause the space to be retained while making the file invisible to most client applications. However, if an ObsoleteLifetime is also specified, then the deleted copy will eventually be eliminated.

As described above, DSM system 10 may incorporate the Fileset feature whereby groups of images associated with a particular customer, project, or transaction are generally stored together on common media. It is noted, however, that multiple images that are associated with one another are stored together in thumbnail and screen resolution versions on short-term media for ease of access, while associated high resolution versions are stored, preferably together, on longer-term media. The fileset feature allows a user to group files into a logical collection, and perform operations on the files as a group.

An example is a group of image files representing images scanned from a single roll of film. The thumbnail and screen resolution versions of each image are stored together with those of associated images in the roll of film to facilitate quick web access to the images. The high resolution versions of the film images can be migrated offline. At the outset, when the images are checked into DSM system 10, the thumbnail, screen resolution, and high resolution images can all be stored on the short-term media, subject to subsequent migration of the high resolution images.

In addition to creating a fileset for a single roll of film, system 10 can be configured to include in the fileset images from multiple rolls of film submitted by a common customer. Also, the fileset could include audio, video, or other content originated by the common customer. Accordingly, filesets can be configured to have their member files reside together on media, so that operations on the fileset, such as archival, migration, retrieval, and deletion, can be performed significantly faster than operating on the individual files, which might otherwise be distributed across multiple media.

DSM system 10 can be further configured to take advantage of metadata associated with each media volume and each file, thereby providing features referred to as media independence and self-describing media. Metadata can be generated for each volume in the form of a file that uniquely identifies the volume with a guid and other useful information. In this case, system 10 may generate the metadata. For individual files, however, it may be desirable for the client application to generate metadata, including a guid and information concerning the particular customer, project, or transaction associated with the file.

In this manner, the client application can pass through to DSM system 10 simply the content of the image file as a blob and the content of the metadata file as a blob. In other words, DSM system 10 need not be concerned with the content of the image/metadata file. Rather, the client application provides sufficient information to the database server, such as a SQL server, to allow DSM system 10 to locate the file and retrieve it for direct access by the client application. The client application is responsible for the format of the image file.

Thus, for a web-based client application, the image file can be converted to a browser-recognizable format prior to submission to DSM system 10. Along with media independence, system 10 may further include a feature whereby volume metadata is stored on each physical volume to track the volume across within a local server or across a network. The metadata can be useful in tracking volumes and files, verification of the identities of loaded volumes, and database recovery.

Figure 7:
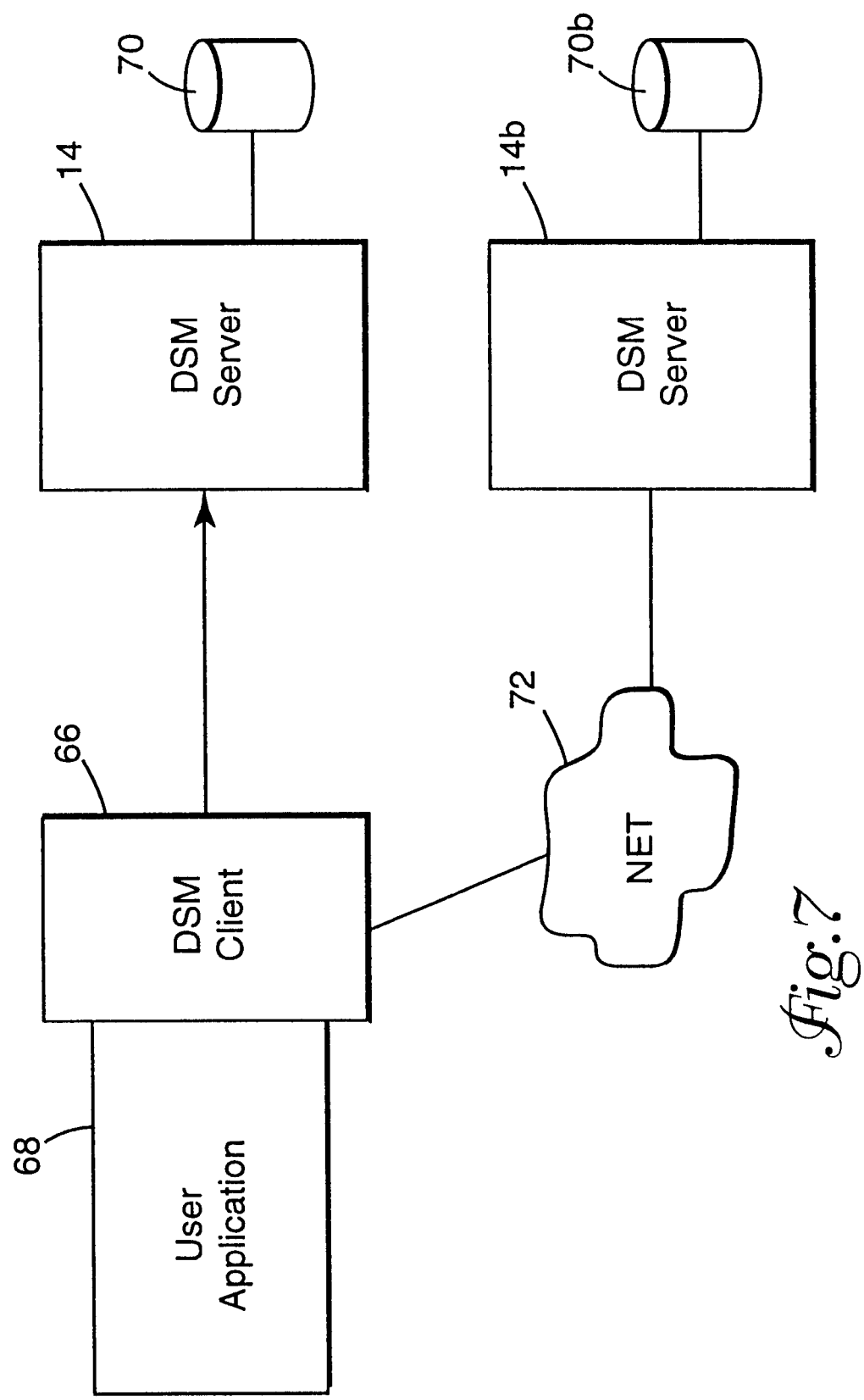
FIG. 7 is a functional block diagram illustrating the interaction between a client application and a server component in a system as shown in FIG. 1.

FIG. 7 is a functional block diagram illustrating the interaction between a client application and a server component in a system as shown in FIG. 1. As shown in FIG. 7, a client application programming interface (API) also can be included to provide a number of features to a programmatic user of the system and method. In particular, DSM client 66 can use the client API to allow for file storage and retrieval by DSM server 14 that is either directed by a user application 68 to or from a particular collection of media 70, or is undirected. Further, the client API can facilitate file grouping by DSM server 14 by allowing fileset creation and modification by user application 68 to generate logical collections of files on storage media 70.

The client API also can be used to provide restricted, password-protected logons to distributed server systems, user and user group permissions on files, and a set of privileged, administrator-only functions. For access to a remote DSM server 14b and the associated collection of media 70b over a network 72, the client API implemented between DSM client 66 and the remote DSM server can provide additional levels of security. For example, the server system can be protected first by a firewall on the server side of the network 72, second by a HSM system server logon and password, third by a file system access control lists, such as the NTFS ACL provided by the Windows NT operation system, and finally by database server logon and password. In addition, the client API enables policy creation and modification to provide settings for determining default behavior of the storage management function and its background agents.

System configuration also can be managed via the client API, such that hardware and software setup is API-configurable. With the client API, the server systems can be local or remote. In particular, the client API implementation can be made to communicate through industry-standard TCP/IP protocols across network 72 to distributed server systems running on any machine that is IP-addressable by the machine on which a user application 68 runs.

The policies implemented by an administrator govern several behavioral aspects of the data and media management functions. For example, policies can be defined to control the set of media 70 to be used for storage of files associated with particular clients, the movement and replication of the files to other sets of media, peer-to-peer data movement between servers, the timing of data movement and replication, maximum file size allowed for various sets of media, retention intervals on various sets of media, versioning, fileset behaviors, media lifetime, tape retensioning, tape compaction, automated media replacement, and automated media upgrades.

Figure 8:
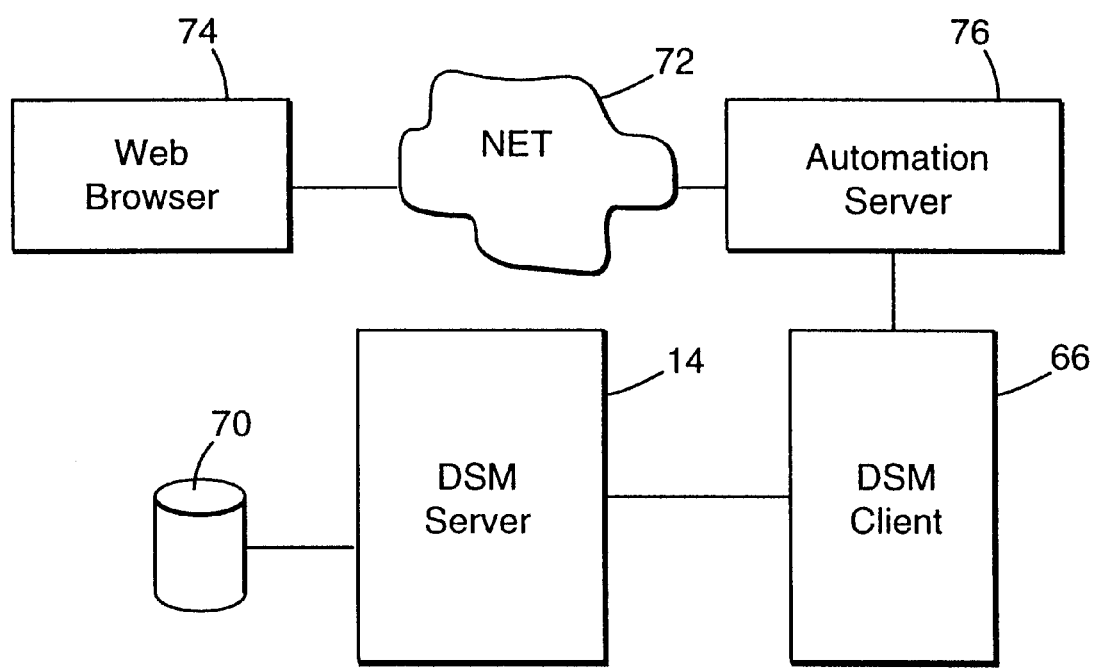
FIG. 8 is a functional block diagram illustrating the interaction between a web-based client application and a server component, via an automation server component that links the client and server, in a system as shown in FIG. 1.

FIG. 8 is a functional block diagram illustrating the interaction between a web-based client application 74 and a DSM server component 14, via an automation server component 76 that links the client application, DSM client 66, and server 14, over a network 72, in a system 10 as shown in FIG. 1. System 10 also can be configured to provide direct access to the storage function instead of indirect access, e.g., via a SQL server. In particular, the system can be arrange to give privileged clients direct read-only access to the file-oriented storage media, with guarantees that the files they specify will remain on that media until they specify otherwise. This provides, for example, the fastest and most direct access to media files that need to be published to web sites for use by web applications 74, by allowing web servers to publish stored files without having to make a copy of the file elsewhere.

This direct access feature also can support specific user-specified file extensions so that web applications 74 that trigger on file extension, can use this feature. As another feature, the system and method may employ an architecture that allows a variety of functions to be allocated to the same or different computer servers in a single storage management system. In order to link web pages applications 74 to the DSM executable programs, system 10 can use an interface referred to as an automation server 76. Automation server 76 is created as prescribed by applicable Microsoft specifications. Various automation servers having features unique to system 10 can be incorporated together or individually as follows:

(1) Storage Automation Server: This aspect of automation server 76 allows a web interface to attach and utilize the client API implemented in DSM client 66 as described above. This interface is portable across any user application that requires a web browser interface 74 to the storage management system 10. Another unique component is the locking down of individual images on a "Hot" cache to avoid migration. Finally, in storing the images, this automation server specifies a file extension to append to a GUID assigned to the file. This provides great advantage when viewing the images from a browser 74 that does not support any type of image file decoding. For example, when viewing an image, the Netscape Navigator web browser only examines the file name extension such as .jpg, .gif, .tif, etc.

(2) Exe Automation Server: This aspect of automation server 76 allows a user to kick off and get a return result from any executable program such as within DSM client 66 and DSM server 14 out of a web browser interface 74.

(3) Image Tool Automation Server: This aspect of automation server 76 allows the calling of image processing tools within DSM client 66 and DSM server 14 from a web browser interface 74.

(4) Event Log Automation Server: Because web interfaces are page driven and stateless, debugging is extremely difficult. This aspect of automation server 76 allows any web interface 74 to log errors encountered from within a web page to the NT event logging facility on any NT server, e.g., DSM server 14,. In this manner, any event at web interface 74 is translated for programmatic delivery to the NT server, and can be logged for analysis.

System 10 also can be configured to facilitate web-based workflow within an web application 74 that invokes the storage management function provided by DSM client 66 and DSM server 14,. From various web pages, and calling the above automation server 76, for example, an application can scan and/or acquire images from a high speed film scanner, photoscanner, flatbed scanner, PCMCIA cards (digital cameras), or any TWAIN compatible device (this is configurable). Those images then can be compressed into three image file types: (1) a thumbnail image, (2) a screen resolution image, and (3) a high resolution image. All three versions of each image are sent and "checked-in" to the storage management function with a file extension known to be processable by web browser 74, e.g., .jpg, via automation server 76.

Thus, the client application supporting the web-based workflow within web browser 74 converts each acquired image to the supported format such that the user can have direct access to the images maintained by the storage management function of DSM server 14 within the web browser. No images need to be kept directly within the client database. The screen resolution and thumbnail versions can be "locked" down by DSM server 14 on the short-term media, such as a RAID, and never allowed to migrate offline to tape. At the same time, the high resolution image may be allowed to migrate according to user-defined migration policies then in effect. In this manner, internet access to the images is as quick as possible. Also, the locked-down images are not stored by the client database server, but rather by the HSM server for direct access by the user. By migrating the high resolution image, however, storage costs for RAID are dramatically reduced. In other words, an application can be configured to store images as economically and efficiently as possible using system 10, with the potential for growth of storage capacity being unlimited and scalable.

As a further feature, system 10 may provide a "digital vault" function within a client application implemented using web browser 74. This function can be supported in part by the fileset feature. With this feature, each consumer has his/her own unique digital vault that is accessible as a web page and resembles an electronic safety deposit box. This digital vault contains images that are categorized and stored in folders that are graphically represented on web page browser 74 as a set of drawers. Each set consists of a single or multiple set of images that were acquired from one of the acquisition devices described above. One set could be a single roll of film, another could be a scanned legal document or documents, another set can be a VHS tape or tape library.

This vault can be password and login protected. All image transmissions can be done under SSL. The vault image viewing is also secured through a virtual directory service, another sequence of logins into the storage management system 10, a Microsoft SQL Server, and the Windows NT NTFS file system itself via ACL. From the vault, the consumer can proof and create his/her own media order. That media order is placed into the a "shopping basket" for the consumer, and totaled for payment and shipping. The consumer may also send those images to a third party via internet mail. Those images stored within the vault are set on an aging algorithm where after a predetermined number of days, the images are deleted from system 10.

The foregoing detailed description has been provided for a better understanding of the invention and is for exemplary purposes only. Modifications may be apparent to those skilled in the art without deviating from the spirit and scope of the appended claims.

What is claimed is:

1. A method for storing files among a hierarchy of data storage media in a hierarchical storage management system, the method comprising:

assigning the files to filesets, each of the files assigned to a respective one of the filesets sharing one or more common attributes with the other files assigned to the respective fileset;

storing the files assigned to the respective fileset together on a common data storage medium at a first level in the hierarchy of data storage media; and moving the files assigned to the respective fileset together from the common data storage medium to another common data storage medium at a second level in the hierarchy of data storage media, such that the files assigned to the respective fileset are stored together on one of the data storage media at substantially all times.

2. The method of claim 1, wherein the one or more common attributes include at least one of a common entity and a common project associated with each of the files assigned to the respective fileset.

3. The method of claim 1, wherein the one or more common attributes include a common transaction associated with each of the files assigned to the respective fileset.

4. The method of claim 1, wherein the files include medical diagnostic imagery, and the one or more common attributes include at least one of a common patient and a common medical practitioner associated with each of the files assigned to a respective one of the filesets.

5. The method of claim 1, wherein the files include advertising imagery, and the one or more common attributes include a common advertising customer associated with each of the files assigned to the respective fileset.

6. The method of claim 1, further comprising retrieving the files assigned to the respective fileset together as a group.

7. The method of claim 1, further comprising deleting the files assigned to the respective fileset together as a group.

8. The method of claim 1, further comprising, in response to a user request to take action with respect to one of the files in one of the filesets, taking the requested action with respect to all of the files in the respective fileset.

9. The method of claim 8, wherein the requested action includes deletion of the respective file, and taking the requested action includes deleting all of the files in the respective fileset.

10. The method of claim 8, wherein the requested action includes retrieval of the respective file, and taking the requested action includes retrieving all of the files in the respective fileset.

11. The method of claim 1, wherein the first level of data storage media includes magnetic hard disk media and the second level of data storage media includes one of optical data storage media and magnetic tape media.

12. A computer-implemented system for storing files among a hierarchy of data storage media in a hierarchical storage management system, the file storage system comprising a processor that is programmed to:

assign the files to filesets, each of the files assigned to a respective one of the filesets sharing one or more common attributes with the other files assigned to the respective fileset;

control storage of the files assigned to the respective fileset together on a common data storage medium at a first level in the hierarchy of data storage media; and control movement of the files assigned to the respective fileset together from the common data storage medium to another common data storage medium at a second level in the hierarchy of data storage media, such that the files assigned to the respective fileset are stored together on one of the data storage media at substantially all times.

13. The system of claim 12, wherein the one or more common attributes include at least one of a common entity and a common project associated with each of the files assigned to the respective fileset.

14. The system of claim 12, wherein the one or more common attributes include a common transaction associated with each of the files assigned to the respective fileset.

15. The system of claim 12, wherein the files include medical diagnostic imagery, and the one or more common attributes include at least one of a common patient and a common medical practitioner associated with each of the files assigned to a respective one of the filesets.

16. The system of claim 12, wherein the files include advertising imagery, and the one or more common attributes include a common advertising customer associated with each of the files assigned to the respective fileset.

17. The system of claim 12, wherein the processor is further programmed to control retrieval of the files assigned to the respective fileset together as a group.

18. The system of claim 12, wherein the processor is further programmed to control deletion of the files assigned to the respective fileset together as a group.

19. The system of claim 12, wherein the processor is further programmed to receive a user request to take action with respect to one of the files in one of the filesets and, in response to the request, take the requested action with respect to all of the files in the respective fileset.

20. The system of claim 19, wherein the requested action includes deletion of the respective file, and the processor is programmed to take the requested action by deleting all of the files in the respective fileset.

21. The system of claim 19, wherein the requested action includes retrieval of the respective file, and the processor is programmed to take the requested action by retrieving all of the files in the respective fileset.

22. The system of claim 12, wherein the first level of data storage media includes magnetic hard disk media and the second level of data storage media includes one of optical data storage media and magnetic tape media.

23. A method for storing files, the method comprising:

storing the files on data storage media volumes;

writing, to each of the media volumes, volume metadata that uniquely describes the respective volume;

writing, with each of the files stored on the media volumes, file metadata that uniquely describes the respective file; and moving one or more of the files from one of the media volumes to another of the media volumes, wherein each of the moved files carries with it the file metadata for the respective moved file.

24. The method of claim 23, wherein each of the volume metadata and the file metadata is based on a globally unique identifier (guid).

25. The method of claim 23, wherein storing each of the files includes storing a data file containing the contents of the respective file and storing a metadata file containing the file metadata.

26. The method of claim 23, further comprising:

constructing original file location database entries specifying the arrangement of the files on each of the media volumes; and in the event the original database entries become corrupted, reconstructing the database entries using the file metadata written with each of the files stored on the respective media volume.

27. The method of claim 26, wherein the file metadata for the files stored on the respective media volume provides sufficient information to reconstruct the database entries access to the original database entries.

28. A computer-implemented system for storing files, the system composing a processor that is programmed to:
   control storage of the files on data storage media volumes;
   write, to each of the media volumes, volume metadata that uniquely describes the respective volume;
   write, with each of the files stored on the media volumes, file metadata that uniquely describes the respective file; and
   control movement of one or more of the files from one of the media volumes to another of the media volumes, wherein each of the moved files carries with it the file metadata for the respective moved file.

29. The system of claim 28, wherein each of the volume metadata and the file metadata is based on a globally unique identifier (guid).

30. The system of claim 28, wherein storing each of the files includes storing a data file containing the contents of the respective file and storing a metadata file containing the file metadata.

31. The system of claim 28, further comprising:
   constructing original file location database entries specifying the arrangement of the files on each of the media volumes; and
   in the event the original database entries become corrupted, reconstructing the database entries using the file metadata written with each of the files stored on the respective media volume.

32. The system of claim 31, wherein the file metadata for the files stored on the respective media volume provides sufficient information to reconstruct the database entries access to the original database entries.

* * * * *